US006696258B1

(12) United States Patent
Wei et al.

(10) Patent No.: US 6,696,258 B1
(45) Date of Patent: Feb. 24, 2004

(54) MESOPOROUS MATERIALS AND METHODS OF MAKING THE SAME

(75) Inventors: Yen Wei, Plainsboro, NJ (US); Danliang Jin, Twinsburg, OH (US); Tianzhong Ding, Wilmington, DE (US); Jigeng Xu, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 09/598,717

(22) Filed: Jun. 21, 2000

Related U.S. Application Data

(63) Continuation of application No. PCT/US99/01116, filed on Jan. 20, 1999.
(60) Provisional application No. 60/071,987, filed on Jan. 20, 1998.

(51) Int. Cl.⁷ ..................... G01N 33/53; G01N 33/543; C01B 37/02; C04B 38/00
(52) U.S. Cl. ............................. 435/7.2; 435/4; 435/7.1; 435/14; 436/518; 436/523; 436/524; 436/528; 423/702; 424/484; 424/489; 424/499
(58) Field of Search .................... 423/702; 424/484, 424/489, 499; 435/4, 7.1, 7.2, 14; 436/518, 523, 524, 528

(56) References Cited

U.S. PATENT DOCUMENTS

| | | | | |
|---|---|---|---|---|
| 4,937,208 A | * | 6/1990 | Yamamoto | 501/12 |
| 5,591,453 A | * | 1/1997 | Ducheyne et al. | 424/422 |
| 5,672,556 A | | 9/1997 | Pinnavaia et al. | 502/63 |
| 5,795,559 A | | 8/1998 | Pinnavaia et al. | 423/702 |
| 5,840,271 A | | 11/1998 | Carrazza et al. | 423/700 |
| 5,849,258 A | * | 12/1998 | Lujano et al. | 423/700 |
| 5,919,430 A | * | 7/1999 | Hasenzahl et al. | 423/702 |
| 5,951,962 A | * | 9/1999 | Muller et al. | 423/702 |
| 6,027,666 A | * | 2/2000 | Ozin et al. | 252/301.4 R |
| 6,054,111 A | * | 4/2000 | Antonietti et al. | 419/2 |

OTHER PUBLICATIONS

G.S. Attard, J.C. Glyde, C.G. Goeltner, "Liquid–crystalline Phases as Templates for the Synthesis of Mesoporous Silica", *Nature* (1995), 378, pp. 366–368.

C.T. Kresge, M.E. Leonowicz, W.J. Roth, J.C. Vartuli, J.S. Beck, "Ordered Mesoporous Molecular Sieves Synthesized by a Liquid–crystal Template Mechanism", *Nature* (1992), 359, pp. 710–712.

N.K. Raman, M.T. Anderson, C.J. Brinker, Template–Based Approaches to the Preparation of Amorphous, Nanoporous Silicas, *Chem. Mater.*, (1996), 8, pp. 1682–1701 and references therein.

J.S. Beck, J.C. Vartuli, W. J. Roth, M.E. Leonowicz, C.T. Kresge, K.D. Schmidt, C.T.–W. Chu, D.H. Olson, E.W. Sheppard, S.B. McCullen, J.B. Higgins, J.L. Schlenker, "A New Family of Mesoporous Molecular Sieves Prepared with Liquid Crystal Templates", *J. Am. Chem. Soc.*, (1992), 114, pp. 10834–10843.

J.C. Vartuli, C.T. Kresge, M.E. Leonowicz, A.S. Chu, S.B. McCullen, I.D. Johnson, E.W. Sheppard, "Synthesis of Mesoporous Materials: Liquid–Crystal Templating versus Intercalation of Layered Silicates", *Chem. Mater.* (1994), 6, pp. 2070–2077.

Q. Huo, D.I. Margolese, U. Ciesla, P. Feng, T.E. Gier, P. Sieger, R. Leon, P.M. Petroff, F. Schüth, G.D. Stucky, "Generalized Synthesis of Periodic Surfactant/Inorganic Composite Materials", *Nature* (1994), 368, pp. 317–321.

H. Yang, A. Kuperman, N. Coombs, S. Mamiche–Afara, G.A.Ozin, "Synthesis of Oriented Films of Mesoporous Silica on Mica", *Nature* (1996), 379, pp. 703–705.

A.D. Firouzi, D. Kumar, L.M. Bull, T. Besier, P. Sieger, Q. Huo, S.A. Walker, J.A. Zasadzinski, C. Glinka, J. Nicol, D. Margolese, G.D. Stucky, B.F. Chmelka, "Cooperative Organization of Inorganic–Surfactant and Biomimetic Assemblies", *Science* (1995), 267, pp. 1138–1143.

A. Monnier, F. Schüth, Q. Huo, D. Kumar, D. Margolese, R.S. Maxwell, G.D. Stucky, M. Kirshnamurty, P.M. Petroff, A. Firouzi, M. Janicke, B.F. Chmelka, "Cooperative Formation of Inorganic–Organic Interfaces in the Synthesis of Silicate Mesostructures", *Science* (1993), 261, pp. 1299–1303.

Q. Huo, R. Leon, P.M. Petroff, G.D. Stucky, "Mesostructure Design with Gemini Surfacants: Supercage Formation in a Three–Dimensional Hexagonal Array", *Science* (1995), 268, pp. 1324–1327.

Q. Huo, D.I. Margolese, G.D. Stucky, "Surfactant Control of Phases in the Synthesis of Mesoporous Silica–Based Materials", *Chem. Mater.* (1996), 8, pp. 1147–1160.

(List continued on next page.)

*Primary Examiner*—Long V. Le
*Assistant Examiner*—Kartic Padmanabhan
(74) *Attorney, Agent, or Firm*—Akin Gump Strauss Hauer & Feld, L.L.P.

(57) ABSTRACT

Mesoporous materials and a method for making such materials is disclosed in which the mesoporous materials are made by forming an aqueous solution having an organometallic compound; adding a solution comprising a pore forming material selected from the group consisting of monomeric polyols, polyacids, polyamines, carbohydrates, oligopeptides, oligonucleic acids, carbonyl functional organic compounds, and mixtures and derivatives of these materials to form a sol get matrix by polycondensation; drying the sot gel matrix; and removing the pore forming material from the dried sot-gel matrix to thereby form a mesoporous material. The mesoporous materials have pore diameters of from about 20 Å to about 100 Å and may be used with a biologically active agent immobilized within the pores of the mesoporous material and introduced into a biological system.

22 Claims, 19 Drawing Sheets

OTHER PUBLICATIONS

C.-Y. Chen, H.-X. Li, M.E. Davis, "Studies on Mesoporous Materials", *Microporous Mater.* (1993) 2, pp. 17–26.

J.M.Kim, J.H. Kwak, S. Jun, R. Ryoo, "Ion Exchange and Thermal Stability of MCM–41", *J. Phys. Chem* (1995), 99, pp. 16742–16747.

S.A. Bagshaw, E. Prouzet, T.J. Pinnavaia, "Templating of Mesoporous Molecular Sieves by Nonionic Polyethylene Oxide Surfactants", *Science* (1995), 269, pp. 1242–1244.

P.T. Tanev, T.J. Pinnavaia, "A Neutral Templating Route to Mesoporous Moleuclar Sieves", *Science* (1995), 267, pp. 865–867.

S.A. Johnson, P.J. Ollivier, T.E. Mallouk, "Ordered Mesoporous Polymers of Tunable Pore Size from Colloidal Silica Templates", *Science* (1999), 283, pp. 963–965.

P. Behrens, "Voids in Variable Chemcial Surroundings: Mesoporous Metal Oxides", *Angew. Chem., Int. Ed. Eng.* (1996), 35, pp. 515–518.

Y. Wei, D. Jin, T. Ding, "Optical Rotatory Silica Materials Prepared via Sol–Gel Processes", *J. Phys. Chem.* (1997), 101, pp. 3318–3323.

K.S.W. Sing, D.H. Everett, R.A.W. Haul, L. Moscou, R.A. Pierotti, J. Rouquërol, T. Siemieniewska, "Reporting Physisorption Data for Gas/Solid Systems with Special Reference to the Determination of Surface Area and Porosity", *Pure & Appl. Chem.* (1985), 57, 603–619.

B.C. Lippens, J.H. De Boer, "Studies on Pore Systems in Catalysts versus The t Method", *J. Catalysis* (1965), 4, pp. 319–323.

P.J. Branton, P.G. Hall, K.S.W. Sing, H. Reichert, F. Schüth, K.K. Unger, "Physisorption of Argon, Nitrogen and Oxygen by MCM–41, a Model Mesoporous Adsorbent", *J. Chem. Soc. Faraday Trans. 1* (1994), 90, pp. 2965–2967.

E.P. Barrett, L.S. Joyner, P.P. Halenda, "The Determination of Pore Volume and Area Distributions in Porous Substances—I. Computations from Nitrogen Isotherms", *J. Am. Chem. Soc.* (1951), 73, pp. 373–380.

Avnir D., et al., "Enzymes and Other Proteins Entrapped in Sol–Gel Materials", *Chem. Mater.* 6, pp. 1605–1614, (1994).

Dave, B.C., et al., "Sol–Gel Encapsulation Methods for Biosensors", *Anal. Chem.* 66(22), pp. 1120A–1127A, (1994).

Izutsu, H. et al., "Preparation and Characterization of L–tartaric Acid–Silica Composites Recognizing Molecular Asymmetry", *J. Mater. Chem.*, 7(8), pp. 1519–1525, (1997).

Wei, Y., et al., "Synthesis of New Organic–Inorganic Hybrid Glasses", *Chem. Mater.* 2(4) pp. 337–339, (1990).

* cited by examiner

MESOPOROUS MATERIALS AND METHODS OF MAKING THE SAME

CROSS-REFERENCE TO RELATED APPLICATIONS

This application is a continuation of copending International Patent Application No. PCT/US99/01116, filed Jan. 20, 1999 and further claims the benefit of U.S. Provisional Application No. 60/071,987, filed Jan. 20, 1998. The entire disclosures of International Patent Application No. PCT/US99/01116 and U.S. Provisional Application No. 60/071,987, each as filed, are incorporated herein by reference.

BACKGROUND OF THE INVENTION

The synthesis of mesoporous molecular materials using pore forming materials or "templates" has emerged as an important area of research. However, currently the most successful of such templates for directing the mesophase formation are surfactants. The choice of such templates is relatively limited and many surfactants, e.g. alkylammonium ions and aikylamines, are costly and toxic, particularly with respect to biologically active agents.

The synthesis of mesoporous materials using surfactants as templates has been studied extensively, and the materials were intended for applications in catalysis, biochemical separation technology and molecular engineering. Surfactants, ionic and neutral have been the most commonly used pore forming materials for directing the formation of mesoporosity. The ionic pathways are based on charge matching between the ionic surfactants and ionic inorganic precursors through electrostatic interaction. Neutral surfactants are theorized to use hydrogen bonding between the surfactants and the precursors to direct formation of mesostructures.

The discovery of the M41S family of mesoporous silicate and aluminosilicate molecular mesoporous materials, or sieves, using surfactant templated hydrothermal sol-gel processes was reported in 1992 by C. T. Kresge et al., *Nature*, "Ordered Mesoporous Molecular Sieves Synthesized By A Liquid Crystal Template Mechanism," vol. 359, page 710 (1992). This discovery drew great interest because of the potential applications of such mesoporous materials as catalysts, catalyst supports, separation media, and host material for inclusion compounds. Numerous mesoporous or nanoporous materials have been synthesized and the pore diameter extended from less than 13 Å for conventional zeolites to about 100 Å and lately up to 300 Å. Many synthetic routes and strategies have been developed to yield a wide diversity of materials of various framework chemical compositions and pore structures. The mostly commonly used templates, however, for directing the mesophase formation have been ionic or non-ionic surfactants. A number of mechanistic pathways have been proposed to account for the formation of nanophase structures, based on the electrostatic interactions and charge-matching for the systems with ionic surfactant templates and the hydrogen bonding interactions for the systems with neutral surfactant templates such as amines and polyethylene oxide (PEO) copolymers. A covalent bonding pathway has also been proposed. In addition, mesoporous materials may also be prepared from interlayer crosslinking of a layered silicate through ion exchange reactions with organic cations.

MCM-41 mesoporous materials have an array of hexagonal arrangements of uniform mesopores of 15 to 100 Å in diameter, which could be controlled by the hydrophobic alkylchain length of ionic surfactants or with the aid of auxiliary organic compounds as spacers. The ionic templates are usually removed by high temperature calcination or ion exchange. Strong electrostatic interactions among the ionic surfactants and the silicate intermediates result in matrices with limited pore wall thicknesses of 0.8–1.3 nm that are influenced little by pH in the synthesis. As a consequence, the materials often have limited thermal stability as evidenced by significant pore contraction or even structure collapse during calcination. Nonetheless, MCM-41 and their analogues have been explored for many applications. They may serve as model adsorbents for the study of gas sorption in mesoporous solids, as catalysts especially when transition metal elements or organic functional groups are incorporated into the framework structure, and as host materials for inclusion of other molecules.

With neutral, primary-amine surfactants as the template, a family of hexagonal mesoporous silicas have been prepared. The pore size may be adjusted by changing the hydrophobic tail length of the amines. The template can be removed by solvent extraction. The mesoporous materials have greater wall thicknesses (1.7–3.0 nm) due to the absence of electrostatic or charge-matching effects, and thus higher thermal stability than M41S materials. However, the materials exhibit both complementary textural and framework-confined mesoporosity. The toxicity of amines also remains a concern if a large scale production is intended.

The use of neutral, polymeric PEO surfactants as pore forming materials has been demonstrated as advantageous in solving the problems of ionic surfactant charge-matching and organic amine toxicity, since the PEO surfactants are neutral, non-toxic and biodegradable. In addition, the pore size can be controlled by varying the size and structure of the PEO surfactant molecules though the channels are largely disordered. Recently, highly ordered porous silicas (20–300 Å) with large wall thickness values of 3.1–6.4 rum and pore volumes up to 2.5 $cm^3/g$ were synthesized by using alkyl PEO oligomeric surfactants and poly(alkylene oxide) block copolymers as templates in strongly acidic media, however, such acidic media are not biocompatible and would present problems with respect to applications involving biologically active agents. In addition, it is difficult to remove such templates using solvent extraction due to their high molecular weight. Further, such attempts do not generally form transparent, monolithic materials which are important for specific applications.

One area of application of microporous and mesoporous materials is for the immobilization of biologically active agents within these materials. Immobilization of enzymes, in particular, has been a subject of extensive research efforts because of its immense technological potentials. Among the popular methods of immobilization is formation of chemical bonding between enzymes and a solid support, which often alters the enzymatic activity. A variety of enzymes and other bioactive substances have been entrapped in inorganic oxides such as silica for biocatalysis and biosensor applications through conventional sol-gel processes. However, because of the microporous nature of the conventional silica matrices (i.e. typical pore diameter<15 Å and pore volume<0.25 $cm^3/g$), the catalytic activities of enzymes are hindered by low diffusion rates of substrate molecules and poor accessibility of enzymes inside the materials.

Mesoporous materials are valuable to the life sciences because the larger pore size in comparison with microporous materials allows for a more suitable environment and better mass transfer for biologically active agents. Much of the prior art involving the immobilization of biologically active agents in porous materials involves use of microporous materials, not mesoporous materials. Biologically active agents previously have been bound to microporous materials, but the pore diameters result in steric hindrance and mass transfer limitations on the use of such materials in biological reactions.

Recent advances in the development of mesoporous materials have enabled the immobilization of biologically active agents, but these techniques primarily involve the use of surfactants as templating agents. The syntheses are either detrimental to the activity of biologically active agents, or employ extreme synthesis conditions (such as high temperature, or low pH). Further, such procedures generally do not provide transparent, monolithic mesostructured materials having immobilized enzymes have been achieved using such methods.

As such, there is a need in the art for an easy-to-synthesize mesoporous material. There is further a need for a process for making such materials, and in which the materials can be biocompatible. There is also a need for a method for immobilizing biologically active agents which enables biologically active agents to fit in the mesopores while also preserving biological activity. Those prior art methods using templating agents have been generally unsuccessful in that the templating agents used in forming the mesoporous materials were toxic or denaturing to the biologically active agents. There is also a need for a transparent, monolithic, i.e., millimeter sized, mesoporous material as such materials are useful for biosensor applications.

Immobilization of enzymes, and other biologically active agents, by entrapment in a gel matrix is based on the occlusion of an enzyme within a constraining structure tight enough to prevent the relatively large protein molecules from diffusing into the surrounding media, while still allowing penetration of the relatively small substrate and product molecules in and out of the matrix. Due to the advantages in their generality, the methods which are widely used for entrapping biologically active agents, include adsorption on an inert support, encapsulation within a semipermeable membrane, covalent crosslinking of the protein molecules or coupling to a support. The successful immobilization of the enzyme alkaline phosphatase by entrapment in silica sol-gel glasses drew great interest and spawned many researches on the sol-gel immobilization of various bioactive species. Since then, enzymes, whole cells, antibodies and other proteins have been immobilized via the sol-gel processing in various ceramic or glass matrices in the form of fibers, thin films, monoliths or granules for biocatalysts and biosensors applications.

However, the conventional sol-gel process for the formation of ceramic or glass materials consists of hydrolysis of a metal alkoxide precursor, typically tetramethylorthosilicate or tetraethylorthosilicate for forming silica, in the presence of an acid or, less often, a base catalyst, followed by the polycondensation of the inorganic intermediates and evaporation of solvents, giving a porous solid gel. This type of air-dried xerogel typically possesses numerous pores or channels well below 15 Å in diameter, depending on the synthesis conditions. Such materials are often used as the host matrices for the encapsulation of various types of chemicals, especially of recent interest being biologically active agents, due to the relatively mild synthesis conditions and easy manipulation. In direct immobilization by entrapment, no chemical bonding is necessary between the host matrix and the guest substance, since the target object is physically imprisoned in the host cages with open channels which allow the reactants and products to migrate through but, ideally, not the entrapped guest. This method is especially suitable for the immobilization of bulky biologically active agents in that no chemical modification of the biomolecules is needed for an effective trapping through primary bonding and the preparation process often involves relatively mild conditions. The resultant ceramic or glass matrix provides a chemically and thermally stable and inert environment for the immobilized species. In addition to the advantages of continuous use and easy separation and recovery of the heterogeneous biocatalyst from the reaction mixture, previous work shows that immobilized enzymes have greater thermal and biochemical stability than the free enzymes in solution.

Despite the advantageous properties of these matrices, however, the problem of internal diffusion-controlled mass transport of the substrate and product inside the rigid sol-gel matrix has been remained a key issue due to limited pore or channel size that is hard to bring under control in the one-step direct immobilization processes previously employed. And consequently, this type of immobilization technique has not been generally used in place of traditional methods for protein and cell immobilization.

After immobilized in a matrix, the enzyme is required to retain at least part of its original catalytic activity. The apparent rate of reaction for immobilized enzymes with their substrates in various organic or inorganic matrices is often found to be diffusion-controlled. This is even a more severe problem for the immobilized enzymes in the highly crosslinked rigid sol-gel materials. This problem is intensified due to the limited accessibility of entrapped enzyme and limited rate of internal diffusion of the substrate due to the narrow matrix pores or channels which are not large enough to eliminate mass transport resistances in the as-synthesized biogels. The kinetic studies may often reflect only the apparent reaction rate of immobilized enzyme with its substrate, which is determined by the rate of internal mass transport rather than by the enzyme-catalyzed reaction kinetics, especially for an enzyme of high activity. In this case, the rate of reaction manifests the diffusion-controlled encounter of the enzyme and its substrate. Therefore, the actual or inherent catalytic activity of immobilized enzyme is hard to determine and is very often underestimated, which easily leads to the conclusion that the enzyme is structurally modified or partially denatured or deactivated during or after immobilization. Also, the internal mass transfer resistances severely limit the practical applications of immobilized enzymes for various occasions such as biosensors where short response intervals are crucial or where macroscopic monoliths are needed.

Therefore, there is a need for improved matrices with larger channels or pore diameters to facilitate the migration of the substrates and products through the pores to adapt such materials for practical applications.

Mesoporous sol-gel materials may be an alternative host for the development of improved biogels. Previously, mesoporous silicate and aluminosilicate, as well as other metal oxides with pore diameters in the range 20 to 100 Å, and up to 300 Å have been synthesized based on the template-directed hydrothermal reactions according to the varied ionic or nonionic surfactant templating pathways. In most cases, the template-based synthesis approaches to the mesostructured materials are difficult to adapt for direct immobilization of biologically active agents due to the severe reaction conditions necessary. Although indirect enzyme immobilization in a mesoporous MCM-41 molecular sieve has been tried, simple, direct immobilization of biologically active agents in such mesoporous sol-gel materials has not yet been achieved.

As discussed above, when an enzyme with high activity is immobilized in a porous matrix, its activity will often be determined by the availability of the substrate in the near vicinity of its surface or active site. The apparent enzymatic reactivity may be limited by the rate of internal diffusion of its substrate in the matrix instead of the kinetics in case of the kinetic reaction rate greater than the diffusion rate. That is, the rate of reaction will be higher if it is not limited by the rate of internal diffusion of the substrate, and sometimes, of the product through the carrier. In the extreme cases, the substrate molecules will never have a chance to encounter the enzyme molecules entrapped in the core of a relatively large particulate because they have already been consumed and converted into the products by the enzyme molecules in the outer shell before they can reach the particle center. This will yield a lowered apparent activity when the calculation is based on the total amount of enzyme entrapped. It is known that volume diffusion proceeds in large pores exceeding 100 nm while Knudsen diffusion proceeds in narrow pores below 100 nm in which the mean free way of the molecules exceeds the pore diameter, and sol-gel materials having pore diameters in the range of micropores (<20 Å) or mesopores (20–500 Å) fall into this category. It has been expected and pointed out that diffusion limited reaction rates have been evident in microporous sol-gel materials and virtually an obstacle in the practical applications.

As such, there is a need in the art for a mesoporous material for use in applications with biologically active agents that can be prepared using a pore forming material that is readily available, non-toxic and inexpensive, and is free from the undesirable effects upon biologically active agents such as denaturation or toxicity. Further, there is a need in the art for a simple, controllable synthesis method of such a mesoporous material, and for immobilizing a biologically active agent within such a mesoporous material in which the biologically active agent can retain an acceptable or high degree of its native activity. In addition, it would be desirable to be able to control the desired pore size and volume of such mesoporous materials for various biologically active agents of different sizes to optimize mass transfer, and to achieve monolithic and transparent materials.

SUMMARY OF THE INVENTION

The invention includes a method for making a mesoporous material which comprises forming an aqueous solution having an organometallic compound, adding a solution comprising a pore forming material to form a sol-gel matrix by polycondensation, drying the sol gel matrix and removing the pore forming material from the dried sol-gel matrix to thereby form a mesoporous material. The pore forming material is selected from the group consisting of monomeric polyols, polyacids, polyamines, carbohydrates, oligopeptides, oligonucleic acids, carbonyl functional organic compounds, and mixtures and derivatives thereof. In a preferred embodiment, the pore forming material is a nonsurfactant, polar compound capable of forming hydrogen bonding.

In one embodiment of the above method, a biologically active agent is added after adding the solution of the pore forming material.

The invention further includes a mesoporous material having pores and formed from a sol-gel matrix comprising a pore forming material and having a surface area of at least about 600 $m^2/g$, a pore volume of at least about 0.5 $cm^3/g$ and an average pore size diameter of from about 20 Å to about 100 Å, wherein at least about 50% of pores in the mesoporous material are mesopores.

The invention further includes a method of using a mesoporous material with a biologically active agent which comprises preparing a mesoporous material having pores from a sol-gel matrix which comprises an organometallic compound and a pore forming material selected from the group consisting of monomeric polyols, polyacids, polyamines, carbohydrates, oligopeptides, oligonucleic acids, carbonyl functional compounds, and mixtures and derivatives thereof, immobilizing a biologically active agent within the pores of the mesoporous material and introducing the immobilized active agent into a biological system.

The invention also includes a mesoporous material comprising pores having an average pore diameter of from about 30 Å to about 60 Å, wherein a plurality of the pores are interconnected within the mesoporous material and a biologically active agent immobilized within the pores.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
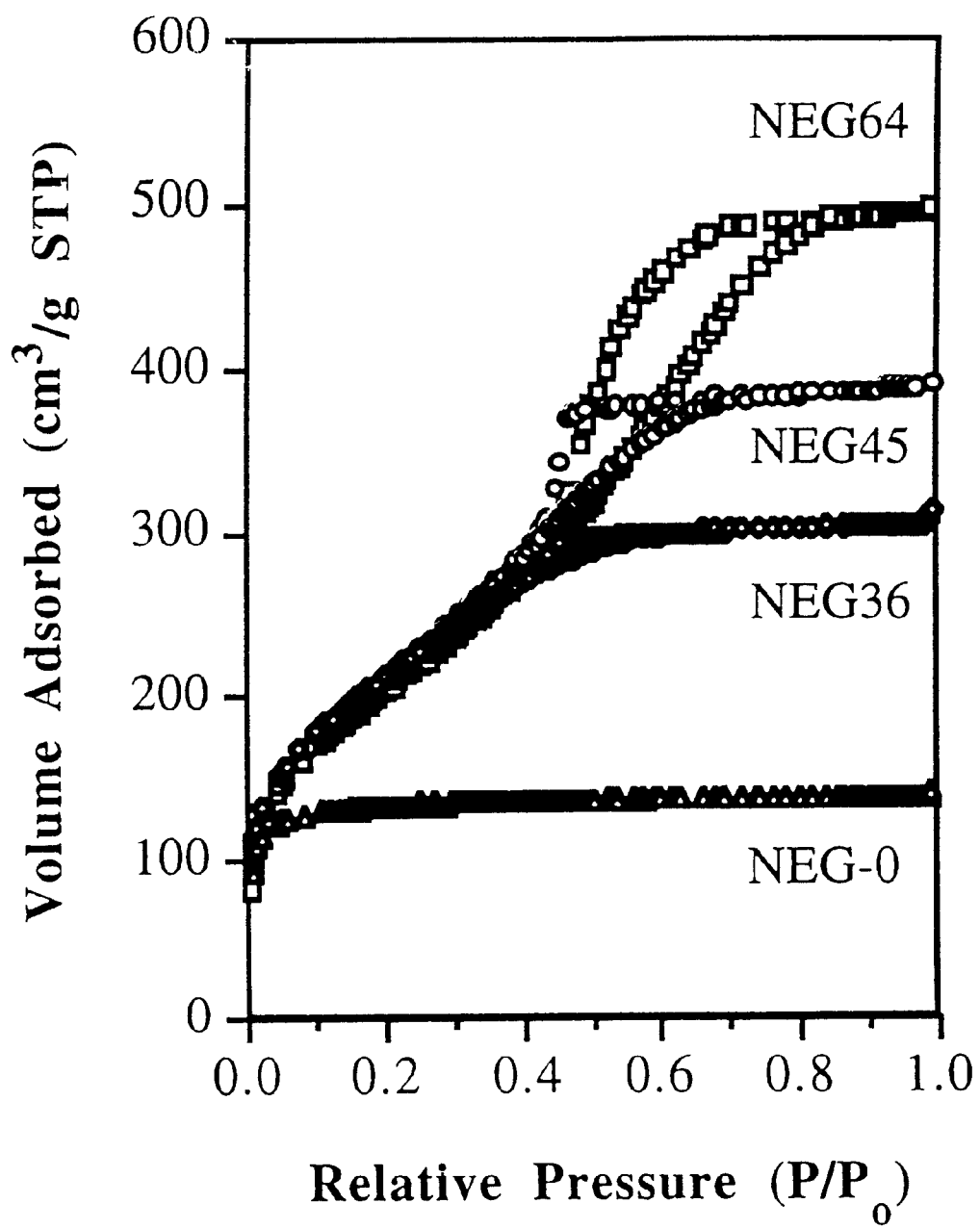
FIG. 1 is a graphical representation of a nitrogen adsorption-desorption isotherm at −196° C. after water extraction for the porous silica samples formed in Example 1 having acid-catalyzed samples.

The following describes preferred embodiments of the invention. However, it should be understood, based on this disclosure, that the invention is not limited by the preferred embodiments described herein. Certain terminology is used herein for convenience only and is not to be taken as a limitation on the present invention. As used herein, an "organometallic compound" means a compound including, at least, a metal element and an organic moiety as described further below. A "sol-gel reaction" includes any reaction for forming a sol-gel matrix, such as processes including hydrolysis of an organometallic precursor in the presence of catalyst and solvent, which may be an aqueous solvent or mixture of organic solvent in aqueous solvent and polycondensation of the inorganic intermediates formed by these reactants to create a porous sol-gel matrix. As used herein, "mesopore" means a pore having a diameter of from about 20 Å to about 500 Å, "macropore" means a pore having a diameter greater than about 500 Å, and "micropore" means a pore with a diameter less than 20 Å. A "mesoporous material" formed in accordance with the invention may include a material which has substantially all mesopores, a material having a mixture of mesopores and micropores, or a material having a mixture of mesopores and macropores. Preferably, the mesoporous materials in accordance with the invention have substantially all pores as mesopores, however mixtures of mesopores with other pores sizes may be formed in accordance with the invention by controlling the amount of pore forming material described below.

The invention includes a versatile, efficient, and preferably biocompatible, non-surfactant method for making mesoporous materials and mesoporous materials having advantageous properties. Non-surfactant, preferably polar, pore forming materials are used in the method such that problems associated with use of surfactants are avoided. Further, pore forming materials are used in the method to provide excellent control over the desired pore diameter and contribute to large surface areas, large pore volumes and narrow pore size distributions in the mesopore range within the mesoporous materials formed by the method. The pore diameter in the mesoporous material can be controlled by varying the concentration of the pore forming material. Such a feature provides flexibility in producing mesoporous materials as well as reproducibility in finished products. By avoiding surfactants, the method does not introduce compounds into the mesoporous structure which affect pore size development and/or which could be toxic to biologically active agents which can be immobilized within the pores of the mesoporous materials.

In addition to novel mesoporous materials and methods for making such materials, the invention further includes a method of using a mesoporous material by immobilizing a biologically active agent within a mesoporous material and introducing it into a biological system. The mesoporous material having a biologically active agent immobilized within the pores allows the biologically active agent to retain from about twice to about 10 times the activity possible using a microporous sol-gel material formed in the absence of a pore forming material for immobilization of a biologically active agent, and in some cases activities of one to three orders of magnitude greater have been observed. Preferably, when immobilizing biologically active agents, the mesoporous material is one in which substantially all of the pores are mesopores.

The invention includes a method for making a mesoporous material which includes, as a first step, forming an aqueous solution of an organometallic compound. This step is directed to initiating formation of a sol-gel matrix. The sol-gel matrix is formed by providing an aqueous solution of the organometallic compound and hydrolyzing it in the presence of a catalyst and preferably a solvent. The hydrolysis is preferably acid or base catalyzed and generates intermediates of the organometallic compound in solution which then undergo polycondensation to form a network or sol-gel matrix. The sot-gel matrix is a composite of organic and inorganic material. Such chemistry is known as sol-gel chemistry and is fully described in Y. Wei et al., *Phys. Chem.*, vol. 101, p. 3318 (1997), which are herein incorporated in full by reference.

The aqueous solution including an organometallic compound, preferably includes an organometallic compound such as an metal alkoxide compound, preferably an alkoxysilane, or a mixture of such compounds. The organometallic compound(s) may be used as the only precursor (s) or used in combination with other sol-gel forming compounds or polymers, including homopolymers and copolymers of styrene, vinyl, acrylic, alkyl acrylate, and the like.

Most preferably, the organometallic compound has the following formula:

$$(R^1)_x-M-(OR^2)_{x-y} \qquad (I)$$

wherein M is preferably a metal capable of forming a sol-gel matrix in aqueous solution; $R^2$ is a branched, straight chain or cyclic alkyl, alkenyl, alkynyl group of from one to 20 carbon atoms or an aromatic group of from six to 20 carbons. $R^1$ is $R^2$, a halogen, or a polymeric moiety such as homopolymers and copolymers of styrene, acrylics, alkyl acrylates, vinyls, and other similar sol-gel forming polymers known in the art or to be developed. In addition, y is less than x and x+y=the valence of M. $R^1$ and $R^2$ may be unsubstituted or fiiher substituted with functional groups which will not interfere with formation of the sol-gel matrix and, preferably, which would not render the matrix toxic or otherwise form too strong a bond with the selected pore forming material. The metal, M, is preferably one of the following metals such as silicon, aluminum, titanium, vanadium, boron, magnesium, iron, niobium and other metals which are useful for forming a sol-gel matrix. More preferably, the metal is silicon, titanium or aluminum, with silicon being most preferred due to the inert nature of these metals with respect to biologically active agents. The valence x+y of the metal M is accordingly preferably 2–6. More than one such organometallic compound may be used to form a mixed sol-gel material, for example, an alkoxysilane and a aluminum alkoxide may be combined to form a mixed matrix of silica and alumina In a preferred embodiment of the first step of the method, the organometallic compound is an alkoxysilane, such as a tetraalkylorthosilicate, and is hydrolyzed. Preferably, a tetraalkylorthosilicate such as tetraethylorthosilicate (TEOS) or tetramethylorthosilicate (TMOS) is used.

The hydrolysis reaction is carried out in an aqueous solution using the above-described organometallic compound, a solvent and a catalyst. If available, commercial solutions of these materials may be used, provided they have acceptable weight percentage ratios, as described below, and satisfy the other criteria as describe herein. The catalyst can be any catalyst capable of initiating a sol-gel hydrolysis/polycondensation reaction, preferably an acid or a base catalyst. Preferred acid catalysts include hydrochloric acid, nitric acid, sulfuric acid, methanesulfonic acid, tolylsulfonic acid, quaternary amines, phosphoric acid, polystyrenesulfonic acid, polymethyacrylic acid, and photoacids which are neutral compounds in the dark and become acids upon exposure to light or radiation. Most preferably, the acid catalyst is hydrochloric acid. Preferred base catalysts include sodium hydroxide, ammonium hydroxide, as well as other Group IA and Group IIA metal hydroxides or alkoxides or salts, for example, carbonate, halide, phosphorate, and acetate salts, triethylamme, and photobases which are neutral in the dark and become basic upon exposure to light or radiation. Suitable solvents are those which are compatible with the sol-gel reactions and which are miscible with or have reasonably good solubility in the aqueous solution. Such solvents include ethers such as tetrahydrofuran, alcohols such as methanol, ethanol, propanol, and butanol, dimethylformamide, dimethylsulfoxide and the like. However, it will be understood, based on this disclosure, that other sol-gel compatible solvents and solvents capable of undergoing hydrolysis may be used.

When a biologically active agent is to be provided and a strong acid or base catalyst is used in the hydrolysis of the organometallic compounds, it is preferred that a neutralizing agent be added after the hydrolysis, such as ammonia and sodium hydroxide or hydrochloric acid or a similar buffering or neutralizing agent, to adjust the pH of the aqueous solution to a range of from about 2 to about 9, and preferably from about 5 to about 8 before adding the biologically active agent. In general, pH is adjusted to the value that is appropriate for optimal stability and activity of the biologically active agent chosen to be immobilized in the sol-gel matrix. Further, the rate of polycondensation reaction is known to be high at a neutral pH of about 7. If pH is already acceptable, the neutralization is not necessary.

In the preferred embodiment, the aqueous solution of the organometallic compound includes the organometallic compound, water, catalyst and solvent. On the basis of one mole of organometallic precursor used, about 0.1 to more than 10 moles, preferably about 1 to 3 moles of water are used, about 0.00001 to 0.5 moles, preferably from about 0.001 to 0.01 moles of catalyst are used, and from about 0.1 or less to about 20 moles, preferably from about 1 to about 5 moles of solvent are used. The most preferred molar ratio of organometallic compound to water to catalyst to solvent is about 0.33:0.82:0.0033:1. The solution is preferably initially mixed and undergoes a pre-hydrolysis reaction in which the mixture becomes homogeneous, but is still liquid. The solution is preferably heated to a temperature from room temperature to the reflux temperature of the solvent, preferably from about 25 to about 100° C. or higher, and most preferably to the refluxing temperature of the solvent, i.e., the boiling temperature of the solvent, preferably under an inert atmosphere such as nitrogen gas. However it will be understood, based on this disclosure, that the hydrolysis temperature may be varied depending on the type of sol-gel to be formed, the catalyst used and the desired pH, among other factors and may be optimized within the ordinary skill in the art to achieve varied results for different applications. Preferably, the material is heated for a period of time sufficient to achieve a high degree of hydrolysis and partial condensation but without gelation, i.e., the losing of fluidity. The refluxing is to facilitate the hydrolysis reaction. Typically, about 1–2 hours is sufficient for this purpose. The solution is preferably then cooled and combined with a solution of one or more pore forming materials. The solution may be cooled by any conventional means, preferably by sitting.

If an acid catalyst is used, the pH can be adjusted at this point as noted above to a desired level, particularly if a biologically active agent is to be immobilized in the mesoporous material. Other auxiliary agents as well known in the art may also be added.

The solution including the pore forming material (also known in the art as a "templating" material) is preferably added after initial pre-hydrolysis as described above. The pore forming material can be a single pore forming material in accordance with the invention or a mixture of such pore forming materials. The pore-forming material, which preferably interacts by polar or hydrogen bonding or other weak bonding interactions with intermediates of the organometallic compound in the pre-hydrolyzed solution is incorporated in the sol-gel matrix formed when the pre-hydrolyzed solution undergoes polycondensation. Polycondensation may occur under acid or base catalyzed or neutral conditions. The sol-gel matrix formed thereby, is then preferably dried by a suitable method to form a solid matrix, which is a solidified matrix formed from the gel. Drying may be accomplished by evaporation, vacuum drying, heating, oven drying, desiccation or other suitable methods, preferably by controlled evaporation over a period of time to allow for a more uniform gelation. In a preferred embodiment, the pore forming material-containing solution is sealed in a container with an impermeable cover such as a paraffin film, having small holes to allow the evaporation of solvents and byproducts of the sol-gel reactions or with a semi-permeable membrane allowing solvent evaporation.

Upon gelation and drying, when using a pore forming material such as those described above, a monolithic disc, typically a transparent, monolithic disc of pore-forming-containing material is obtained. The disc shape is formed by allowing the material to dry in a cylindrical container or mold, however, the shape of the material is not essential to the method as described herein. Evaporation may occur over a period of days, preferably from about 1 to about 10 days, more preferably from about 1 to about 7 days, and most preferably from about 1 to about 3 days. By using a covered container, as described above, volatile solvents and volatilizable unwanted byproducts formed in the sol-gel reaction can thereby be removed by evaporation. While evaporation is preferred, it will be understood, based on this disclosure that various means of drying the sol-gel matrix can be used provided the volatile compounds are separated without substantially affecting the uniformity or consistency of the sol-gel matrix.

The pore forming material is preferably a biocompatible, non-surfactant material which is also compatible with a biologically active agent if such an agent is to be immobilized in the mesoporous material.

In one embodiment, it is preferred that the pore forming material is a non-surfactant, polar solid or high boiling liquid. Most preferably, it is capable of forming hydrogen bonding. Such compounds include, for example, monomeric polyols, polyacids, polyamines, carbohydrates, oligopeptides, oligonucleic acids, and mixtures and derivatives thereof.

"Monomeric polyols" are aliphatic or aromatic polyols of from about 3 to about 20 carbon atoms such as glycerol, ethylene glycol, diethylene glycol, dihydroxyethyl ether, and bisphenol A.

Polyacids may be aromatic or aliphatic and include tartaric acid, EDTA, EGTA, poly- or oligo-styrenesulfonic acid or methacrylic acid, camphorsulfonic acid, oligophosphoric acids and their derivatives.

Polyamines may be aromatic or aliphatic and include diaminoethylamine, triaminoethylamine, diaminoaryl ether, and derivatives thereof.

Carbohydrates which may be used include sugars such as glucose, maltose, fructose, sucrose, lactose, talose, galactose and the like as well as other di-, tri- and oligo-saccharides and complex carbohydrates such as starches. Oligopeptides which may be used include amino acids, dimers, trimers and higher oligomers of peptides. Oligonucleic acids may include AMP, ADP, ATP and other oligomers of nucleotides and their derivatives. Other organic compounds that include carbonyl groups capable of forming hydrogen bonds such as ketones, aldehydes and esters may also be used as the pore forming materials. Derivatives of the above-mentioned pore forming materials include multifunctional compounds with mixed alcohol, amine, acid and carbonyl groups which may be used as well. The pore forming material may be used alone or in combinations of two or more pore forming compounds. Among the above materials, the preferred pore forming materials include D-glucose, D-maltose, D-fructose, sucrose, dibenzoyl-L-tartaric acid, cyclodextins, and soluble starch.

The pore forming material may be added alone or in an aqueous or other solution miscible with the pre-hydrolyzed solution formed as described above. The amount of the pore forming material is preferably from about 20 to about 70% by weight based on the weight of the final, dried pore-forming material-containing solid matrix as determined by theoretical calculation based on the reactants selected for forming the sol-gel matrix in accordance with the ordinary skill in the art. The amount of pore forming material provided can be varied to control the size and number of mesopores within the resulting matrix. The pore forming material may be added at any time prior to the gelling or drying of the sol gel matrix, but it is preferably added after forming the pre-hydrolyzed solution as noted above, followed by neutralizing of the hydrolyzed solution when a biologically active agent is provided in order to minimize unwanted side reactions. An aqueous solution is preferred, because the polarity of the solution solubilizes the pore forming material. While water is preferred, less polar solvents can be used for solubilizing pore forming materials having low polarity provided such solvents are miscible with the pre-hydrolyzed solution. Examples of preferred solutions of pore forming materials include aqueous solutions of D-glucose (0.8 mol/L) and D-maltose monohydrate (1.2 mol/L) and an ethanol solution of dibenzoyl-L-tartaric acid (DBTA) (0.3mol/L) preferably formed while stirring. When using water as a solvent throughout the sol-gel matrix formation, it is preferred that the water used be distilled and/or deionized water to avoid impurities. It is further preferred that the solution be stirred while adding the pore forming material.

The step of adding a pore forming material prior to the gelling or drying and formation of a sol gel matrix both enhances the speed of the overall method of making a mesoporous material and provides the very valuable means for controlling the nature of the pores, i.e., the degree of mesoporosity, and the average pore diameter of the resulting material to narrow ranges such as from about 30 Å to about 60 Å. By adjusting the concentration of pore forming material added, the pore size of the resulting pores can be controlled to achieve pores which are substantially all mesopores, which are a mixture of mesopores and micropores, or which are a mixture of mesopores and macropores for different matrix applications. This can be accomplished by varying the concentration of pore forming material. For example, if a solution of dibenzoyl-L-tartaric acid is added, by varying the amount of dibenzoyl-L-tartaric acid from about 40 to about 60 wt % a mesoporous material can be formed having varied degrees of mesoporosity or pore volume from about 0.6 to about 1.0 $cm^3/g$, and varying ranges of pore diameter of from about 34 to about 60 Å. Examples of this method of controlling resulting pore diameter size and properties of the mesoporous material are set forth below in the Examples.

The method as described above, using the preferred pore forming materials provides a faster route to mesoporous materials than previously obtained in the art by methods which do not use pore forming materials or "templates" and provides a biocompatible, non-toxic mesoporous material which may be used with biologically active agents. The speed of the drying step alone is carried out in as little as from about 1 to about 3 days.

The method further provides a simple, reliable and reproducible procedure for exerting substantially tight control over pore size diameter and degree of mesoporosity in the resulting mesoporous material, and also provides better control of pore diameter range in pore size distribution.

After forming the dried matrix as described above, the pore forming material may be removed from the solid matrix by any suitable purification method which would no have a detrimental effect on the matrix, but which will allow for separation of the particular pore forming material used.

Preferred purification methods involve procedures known to those skilled in the art or to be developed, and include, but are not limited to calcination and solvent extraction. Most preferably, solvent extraction is used. Preferably, to subject the matrix to solvent extraction, the matrix first undergoes grinding to form a particulate form of the matrix, most preferably a powder. Preferred extraction can be undertaken with compatible, preferably polar and low boiling solvents including lower molecular weight alkanols, such as methanol, water, saline and buffered solutions. The solvent can be varied to achieve good removal of the pore forming material depending on the type of pore forming material used. Preferably the solvents, mixtures of the solvents and extraction conditions are selected so as not to be capable of denaturing biologically active materials, when such materials are to be mobilized within the mesoporous material. Multiple extractions can be carried out by a method such as mixing the ground solid matrix with solvent, separating by centrifugation and decanting to substantially remove the pore forming material. Other extraction or purification techniques may be employed.

Because most of the preferred pore forming materials are readily soluble in water, this step provides a simple and efficient means for effectively removing the pore forming material. In this embodiment of the invention, the pore forming material is effectively removed to result in a mesoporous material. The degree of removal of pore forming material can readily be monitored by conventional analytical methods such as infrared spectroscopy or thermogravimetric analysis.

Because most of the pore-forming materials used in this invention are biocompatible, complete and total removal is not necessary even when a biologically active agent will be immobilized within the mesoporous material as in the method described below. This is another advantage of the present invention over existing methods which use surfactants or other materials which are denaturants to biologically active agents such that total removal must be effected increasing the cost of purification and processing.

The invention includes mesoporous materials, which may be either substantially mesoporous, or materials having mixtures of mesopores and micropores, or mesopores and macropores. In any case, the mesopores can be controlled so as to provide a mesoporous pore volume of at least about 0.5 cm$^3$/g, and an average mesoporous average pore diameter of from about 20 Å to about 100 Å, more preferably from about 30 Å to about 60 Å. Most preferably, the mesoporous materials have substantially all mesopores, i.e., they have at least about 50 % mesopores. Preferably the materials are formed using sol-gel techniques, such as those described herein, however, the sol-gel technique should not be considered limited to those described herein, provided that the technique used includes the preferred pore forming materials described above to form the mesopores.

The invention also includes a method for making a mesoporous material and for using a mesoporous material in which a biologically active agent is immobilized within the mesoporous material. The mesoporous material may be any mesoporous structure formed in accordance with this invention or as described herein provided the mesoporous material is formed using an organometallic compound, such as those described above, and a pore forming material as set forth herein, more preferably, using a monomeric polyol, carbohydrate, oligopeptide, oligonucleic acid, a carbonyl functional compound and mixtures and derivatives thereof. While all of the pore forming materials can be used as set forth herein, the above-listed compounds are more preferred for immobilizing a biologically active agent due to the sensitivity of such agents to the polyacids and polyamines, as well as amine-functional compounds.

The mesoporous material is preferably formed by the above preferred sol-gel technique, or by any known sol-gel technique or technique to be developed provided the pore forming material is a preferred pore forming material as set forth herein, i.e., a monomeric polyol, a polyacid, a polyarnine, a carbohydrate, an oligopeptide, an oligonucleic acid, and mixtures and derivatives of these materials.

The biologically active agent to be immobilized within the mesoporous material may be any type of cell, a portion of a cell, a microorganism, a virus, a nucleic acid, an enzyme, a polysaccharide, a polypeptide, a subunit of a polypeptide, a drug, a therapeutic agent, a diagnostic agent and or mixtures or derivatives of these compounds, so long as the agent has biological activity or activity in a biological system. Preferably, the biologically active agent may be immobilized, i.e., entrapped within the pores, by providing the biologically active agent to the sol-gel matrix while the matrix is being formed. However, it will be understood, based on this disclosure, that the biologically active agent can be provided to the mesoporous pores after formation of the matrix and removal of the pore forming material. It is preferred, however, that the biologically active agent is added during formation of the pore forming material, and more preferably, after adding the pore forming material. If an acid-catalyzed method is used, it is preferred that a neutralizing step be undertaken as described above, before introducing the biologically active agent.

After drying and purifying the resulting sol-gel matrix to remove the pore forming material and form the mesoporous material, pores will be formed which will entrap the biologically active agent in the mesoporous material, but will allow sufficient porosity for movement within the pore structure to allow material to diffuse inward and outward thereby providing excellent mass transfer properties and good biological activity from the biologically active agent because the mesoporous material is non-toxic. Further, the method allows for adjustment of pore size to control activity or to adjust pore size for different sized biologically active agents. As such, the method is valuable because it results in an immobilized, but still highly active, biological agent entrapped within a mesoporous material which can be used in a wide variety of applications including diagnostic, therapeutic and catalytic applications.

The great value of this method is that it results in a material that overcomes the primary problems and limitations of immobilizing biologically active materials. The method and resulting materials minimize restriction of access to substrates or other molecules necessary for biological activity caused by steric hindrance due to pore diameters being too small, because pore size may be adjusted to overcome this difficulty. Further pore size can be adjusted for maximized mass transfer properties. In addition, by being able to control pore size, leaching and escape of the immobilized agent due to a too large pore diameter can also be avoided. As the mesoporous materials and the pore forming materials used in the invention are non-toxic, problems associated with toxicity, denaturation or loss of biological activity due to contact with templating or other pore forming materials which are not biocompatible are further obviated. In addition, mesoporous materials with immobilized biologically active agents in accordance with the invention are stable and may not cause denaturation or degradation when exposed to or contacted with physiological elements present in biological systems such as protease, antibodies, and immune system responses or caused by poor thermal stability. As such, the mesoporous materials overcome significant obstacles in the prior art for adopting mesoporous materials for use with biologically active agents.

In one preferred embodiment described herein, the biologically active agent is an enzyme such as acid phosphatase, alkaline phosphatase or horseradish peroxidase. However, as noted above, other biologically active agents may also be used. Preferably, the biologically active agent is added after adding the solution containing the pore forming material but simultaneous addition or addition prior to the pore forming material is also acceptable, provided the biologically active agent retains its activity. For example, if acid catalysis is used in the first step, the biologically active agent will usually have to be added after the neutralization step to prevent denaturation and loss of activity. The enzyme can be added as a stock solution and concentrations of agent in solution can be varied using techniques known to those of ordinary skill in the art depending on the biologically active agent chosen, its expense, availability, the targeted application of use for the biologically active agent and the like.

This method results in the formation of a mesoporous material with an immobilized biologically active material which substantially or completely retains its natural activity. This immobilized agent in this mesoporous material is now ideally suited for catalytic, diagnostic and/or therapeutic applications in biological systems. It has the advantages of a biologically active agent which displays a high degree of thermal stability, for example significant thermal stability is shown at 50° C. as noted in Table 4 below, and also in Table 5, and a network of mesopores, in which a plurality of the pores are interconnected. The pores have diameters sufficient to allow for good mass transfer of substrates and reactants to and from the biologically active material but small enough to prevent leaching and provide a protective cage from degradation by physiological processes.

This invention thus provides a way to obtain biological activities from about twice to about 10 times, and some cases from 1 to 3 orders of magnitude greater than the activity possible using a microporous sol-gel material formed in the absence of a pore forming material for immobilization of a biologically active agent. Since there are no toxic surfactants or other denaturing chemicals used, the native structure of the biologically active material is maintained, and the materials may be formed easily, reproducibly and controllably to form preferred mesoporous structures for various sized biologically active agents.

The preferred pore forming materials result in the property of the pore forming material being readily removable from the matrix. The preferred compounds are readily soluble in aqueous buffers and more importantly, their biocompatibility, in contrast to surfactants which are often denaturants or toxic to biological materials, enables the simultaneous immobilization of biologically active agents in the presence of the pore forming materials.

In introducing a mesoporous material having a biologically active agent immobilized therein, the method further involves contacting the immobilized active agent to a biological system, such as in a human, an animal or an in vitro test specimen. Once in the biological system, the immobilized biologically active agent in the mesoporous material can be used to function as a biosensor, biocatalyst, therapeutic agent and/or a diagnostic agent as well as in any other application in which improved mass transfer, thermal stability and improved biologically active agent activity would be beneficial.

EXAMPLE 1

Tetraethylorthosilicate was purchased from Aldrich, Milwaukee, Wis. Ethyl alcohol was supplied by Pharmco Products of Brookfield, Conn. D-glucose, sodium hydroxide and hydrochloric acid were obtained from Fisher Scientific, Fair Lawn, N.J. All chemicals and reagents were used as received without further purification. The preparation of mesoporous silica-based materials were undertaken as described below.

Various sol-gel reactions were carried out to form mesoporous silica-based materials by using varied D-glucose concentrations. As an exemplary description of the procedure, for forming the 45 weight percent glucose material, the sol-gel reactants included 0.15 mol of tetraethylorthosilicate, 0.46 mol ethanol, 0.375 mol water and 1.5 mmol (2.0 M) hydrochloric acid as an acid catalyst. These components were mixed in a flask at room temperature under agitation. After about 15 minutes, the mixture became homogeneous accompanied by a temperature increase. The solution was heated to reflux under nitrogen atmosphere for 2 hours and cooled to room temperature to form a prehydrolyzed sol. The prehydrolyzed sol formed a stock solution useful for the subsequent synthesis with varied D-glucose levels. The sol, in an amount of 4.0 g, was neutralized with 0.32 ml of 0.25M NaOH (aqueous) to a pH of 6.0. After neutralizing, the sol was combined with a solution of 0.5 g D-glucose in 0.5 g distilled water under stirring. The amount of sol used varied with the desired weight percentage D-glucose. The glucose-containing homogeneous sols formed were sealed in a cylindrical glass container using a paraffin film. From 10–12 small holes were punched with a syringe needle through the film to allow evaporation of volatile molecules of solvents and byproducts of the sol-gel reactions. Upon gelation and drying at room temperature for periods of time of from 3 to 7 days, a transparent and monolithic disc of glucose-containing silica sample was obtained.

To prepare the mesoporous silica-based materials, the as-synthesized samples (which were from 0.3 to 0.9 g, depending on the glucose content) were ground into a fine powder, and immersed in 15 mL distilled and deionized water under agitation for 15 min. After centrifugation and decantation, the samples were placed in another 15 mL of water for 3 hours under agitation. The sample mixtures were centrifuged and the samples were soaked in 15 mL water overnight. In the following two days, the samples were washed twice a day in the same manner. After such an extraction, with a total of about 100 mL of water in seven portions, the samples were dried in an oven at 115° C. overnight. Both infrared and thermogravimetric analysis measurements showed the removal of glucose was complete.

The D-glucose concentration in the sol-gel materials were determined from the weight loss at 750° C. using thermogravimetric analysis (TGA) on a DuPont 2000 Thermal Analyzer equipped with a TGA 950 Module. The samples were first crushed with a mortar and pestle into a fme powder of 100–500 microns particle size. Upon drying at 115 ° C. for 2 hours in an oven prior to TGA. The powdered samples were loaded to the TGA sample container and heated from ambient to 800° C. at a heating rate of 10° C./min under oxygen atmosphere. The infrared spectra of the samples were measured in the form of KBr powder-pressed pellets on a Perkin Elmer 1600 FT-IR spectrophotometer (Norwalk, Conn.) under ambient conditions. Both as-synthesized and water-extracted powder samples were used for the spectral measurements. The nitrogen-sorption characterization of the powdered samples before and after removing D-glucose by extraction were conducted on a Micromeritics ASAP 2010 Surface Area Pore-Size Analyzer (available from Micromeritics of Norcross, Ga.) at −196° C. (liquid nitrogen). The samples were degassed at 200° C. and $10^{-6}$ torr overnight prior to nitrogen-desorption measurement. The surface and pore parameters were calculated using software from Micromeritics, Inc. The simple average pore diameter calculated from $V/S_{BET}$ by the Brunauer-Emmett-Teller (BET) method. The pore diameter using the Barrett-Joyner-Halenda (BJH) pore size distribution method was determined from the maxima of the BJH desorption pore size distribution curve using the Halsey equation. The micropore area and volume were determined by the t-plot method.

The compositions of the glucose-containing silica materials prepared by sol-gel reaction and the pore parameters of the porous silicas upon removal of D-glucose using water extraction are summarized below in Table 1 as inventive Examples NEG15–NEG64. The control sample was formed as set forth above without the pore foming material and data measured without solvent extraction prior to BET measurement (NEG0') and after solvent extraction (NEG0).

EXAMPLE 2

The same procedure as set forth above was undertaken, but used sodium hydroxide as a base catalyst for the hydrolysis and/or polycondensation in the formation of the sol-gel matrix. In preparation of a series of samples, identical amounts of sodium hydroxide were used in place of hydrochloric acid and the same procedure as described in Example 1 was carried out. However, the neutralizing step was not necessary. Varied amounts of 50 weight percent D-glucose solutions were combined with the sol-gel solutions formed with sodium hydroxide. After drying the matrix, transparent, monolithic glucose-containing silica gels were obtained as as-synthesized samples in the same manner as Example 1. The results for the sodium hydroxide samples are also set forth below in Table 1 as samples BEG15–BEG 64.

In both Example 1 and Example 2, at high concentrations of D-glucose, the samples sometimes broke into smaller, but still transparent and crack-free pieces during drying. Control samples for Example 2 were also as noted above in Example 1 (samples BEG0' and BEG0). To remove the D-glucose, the as-synthesized samples were ground to fine powders and extracted with a large amount of distilled water at room temperature. The extent of template removal was monitored by infrared spectroscopy and by TGA after extraction.

The compositions, as represented by the glucose concentrations in the as-synthesized materials, calculated from the feed stoichiometry are comparable to those determined from TGA experiments. The small discrepancies could be attributed to incomplete sol-gel reactions or incomplete removal of moisture. The results from nitrogen adsorption-desorption measurements show that addition of D-glucose as the pore forming material in the sol-gel reactions under basic or near neutral conditions modified the microstructure of silica matrices leading to mesoporosity, similar to that achieved using acid catalysis.

Figure 2:
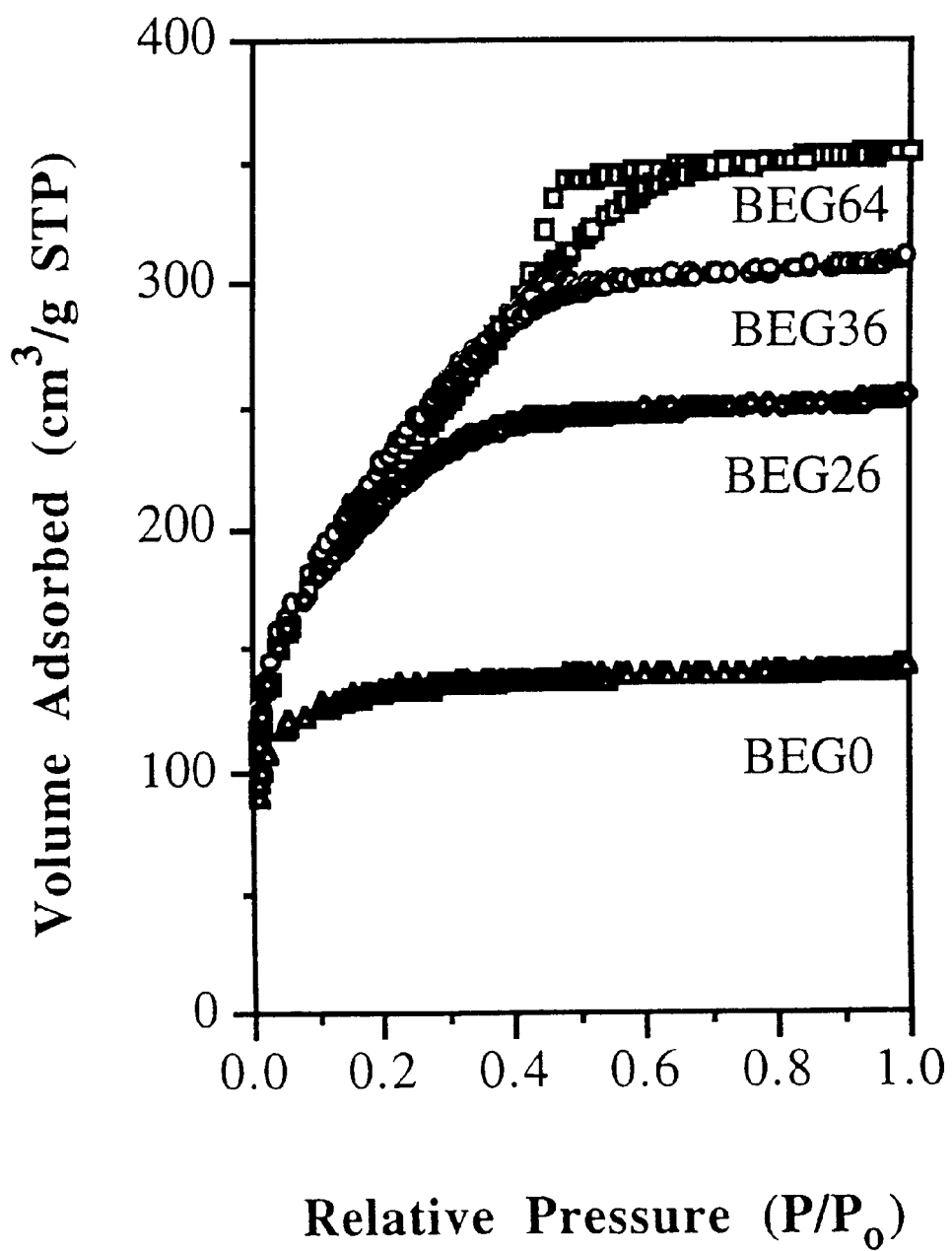
FIG. 2 is a graphical representation of a nitrogen adsorption-desorption isotherm at −196° C. after water extraction for the porous silica samples formed in Example 2 having base catalyzed samples.

The nitrogen adsorption-desorption isotherms at –196° C. for the porous silica samples after water extraction are shown in FIGS. 1 and 2. The control samples (NEG0 and BEG0) prepared using acid and base catalysts without the pore forming material exhibit reversible Type I isotherms, which are typical of xerogels with microporous structures. With increasing concentration of D-glucose, the nitrogen sorption isotherms gradually transform from reversible Type I to Type IV isotherms with H2 hysteresis. The H2 hysteresis loop becomes greater in magnitude and shift to higher relative pressures ($P/P_o$). At the glucose content of 36 wt % and higher, the materials have high surface areas (about 800 m$^2$/g) and pore volumes ($\geq 0.5$ m$^3$/g), indicative of mesoporosity, and show Type IV isotherms with H2 hysteresis loops at $P/P_o$ of about 0.4 to about 0.8. There is a well-defined plateau following the loop at $P/P_o > 0.8$, suggesting the occurrence of pore filling by capillary condensation of nitrogen in the framework-confined mesopores instead of adsorption in the interparticle textural pores. The BET surface areas shown in Table 1 were calculated using the Kelvin equation and were found to increase with D-glucose concentration, up to around 800 m$^2$/g at 45 wt % and then remain relatively unchanged. The pore volume obtained at $P/P_o$ of about 1 continues to increase with D-glucose concentration. It is noted that at high glucose concentrations, it becomes much harder to obtain homogeneous, crack-free samples. When more than 64 wt % of D-glucose was added, separation of glucose from the gels during the drying process was observed.

The as-synthesized samples before removing D-glucose exhibit different types of nitrogen isotherms depending on the amount of glucose in the composites. In general, an

TABLE 1

| | D-glucose Content (Wt %) | | Surface Area ($S_{BET}$) | Pore Volume (V) | BET Pore Diameter | BJH Pore Diameter | Micropore | |
|---|---|---|---|---|---|---|---|---|
| | | | | | | | Area (cm$^2$/g) | Vol (cm$^3$/g) |
| Sample | Calc | Found | (cm$^2$/g) | (cm$^3$/g) | (Å) | (Å) | | |
| NEG0 | 0 | 7.9 | 378 | 0.214 | 22.6 | <17 | 314 | 0.174 |
| NEG0' | 0 | — | 334 | 0.197 | 23.6 | <17 | 285 | 0.158 |
| NEG15 | 15 | 19.1 | 557 | 0.311 | 22.3 | <17 | 295 | 0.166 |
| NEG26 | 26 | 29.1 | 698 | 0.402 | 23.1 | <17 | 49 | 0.026 |
| NEG36 | 36 | 37.0 | 756 | 0.483 | 25.6 | <17 | — | — |
| NEG45 | 45 | 45.3 | 772 | 0.603 | 31.3 | 34.0 | — | — |
| NEG58 | 58 | 58.3 | 749 | 0.629 | 33.6 | 34.8 | — | — |
| NEG64 | 64 | 62.5 | 740 | 0.767 | 41.5 | 34.9 | — | — |
| BEG0 | 0 | 7.1 | 389 | 0.222 | 22.8 | <17 | 281 | 0.157 |
| BEG0' | 0 | — | 395 | 0.227 | 23.0 | <17 | 308 | 0.172 |
| BEG15 | 15 | 18.8 | 652 | 0.369 | 22.6 | <17 | 164 | 0.094 |
| BEG26 | 26 | 28.1 | 712 | 0.394 | 22.1 | <17 | 103 | 0.057 |
| BEG36 | 36 | 37.1 | 813 | 0.482 | 23.7 | <17 | — | — |
| BEG45 | 45 | 43.7 | 837 | 0.545 | 26.0 | 31.5 | — | — |
| BEG52 | 52 | 53.2 | 789 | 0.540 | 27.4 | 31.9 | — | — |
| BEG64 | 64 | 62.0 | 793 | 0.549 | 27.6 | 32.2 | — | — | increase in amount of glucose up to 45 wt % leads to a decrease in surface area and pore volume. The control samples show similar Type I isotherms, surface areas and pore volumes as those after extraction as listed in Table 1. Apparently, the water-extraction procedures may have little effect on the silica structure. For the samples with increasing D-glucose content from 15 to 36 wt % or higher, the nitrogen absorption isotherms changed from Type I to Type II with H4 hysteresis, which is typical of nonporous solids. The lack of porosity is further evidenced by the very small values of specific surface area (<5 m$^2$/g) and pore volume (about 0.005 cm$^3$/g). The t plot analysis shows that these values, however small, are mainly contributed from exterior surface and voids of the sample powders. These observations indicate that in the as-synthesized samples, the silica matrix and D-glucose molecules form close contact, intermingled composites without internal pores detectable by the nitrogen adsorption method.

Figure 3:
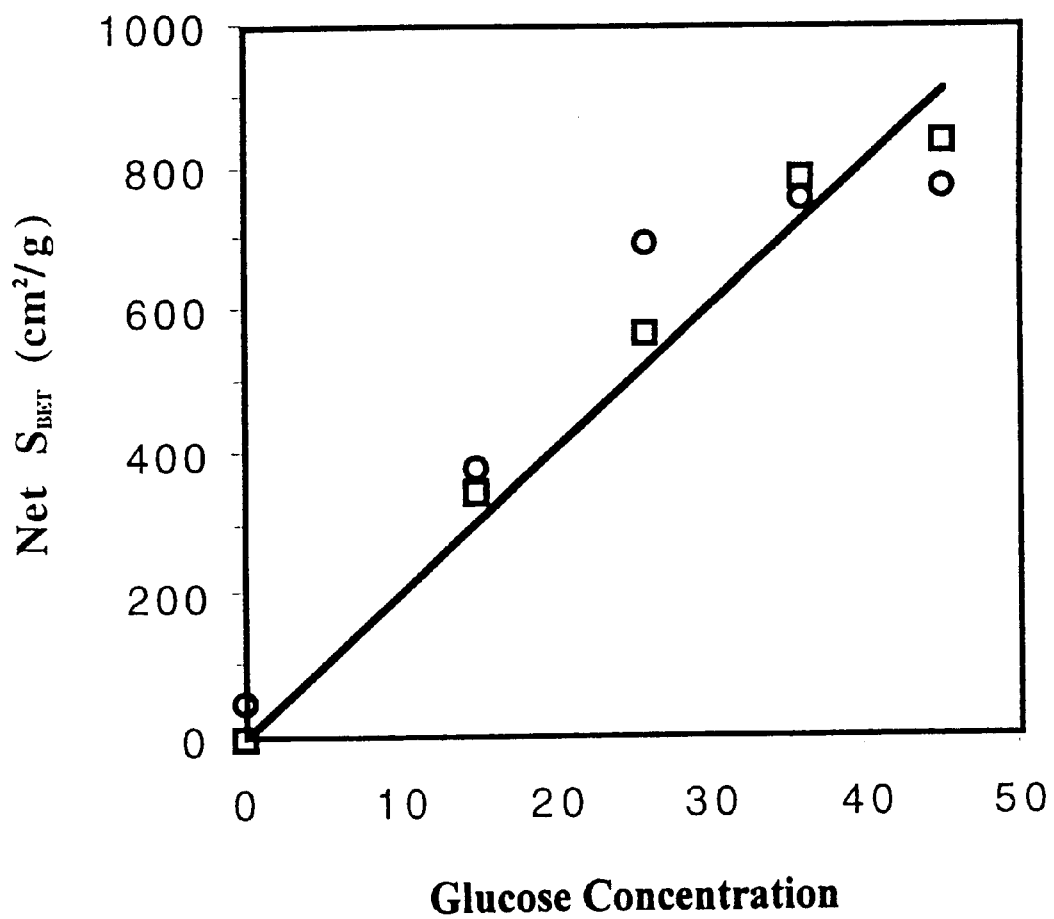
FIG. 3 is a graphical representation of the relationship between the net surface area and glucose concentration after water-extraction for both acid and base catalyzed samples of Example 1 (○) and Example 2 (□)
Figure 4:
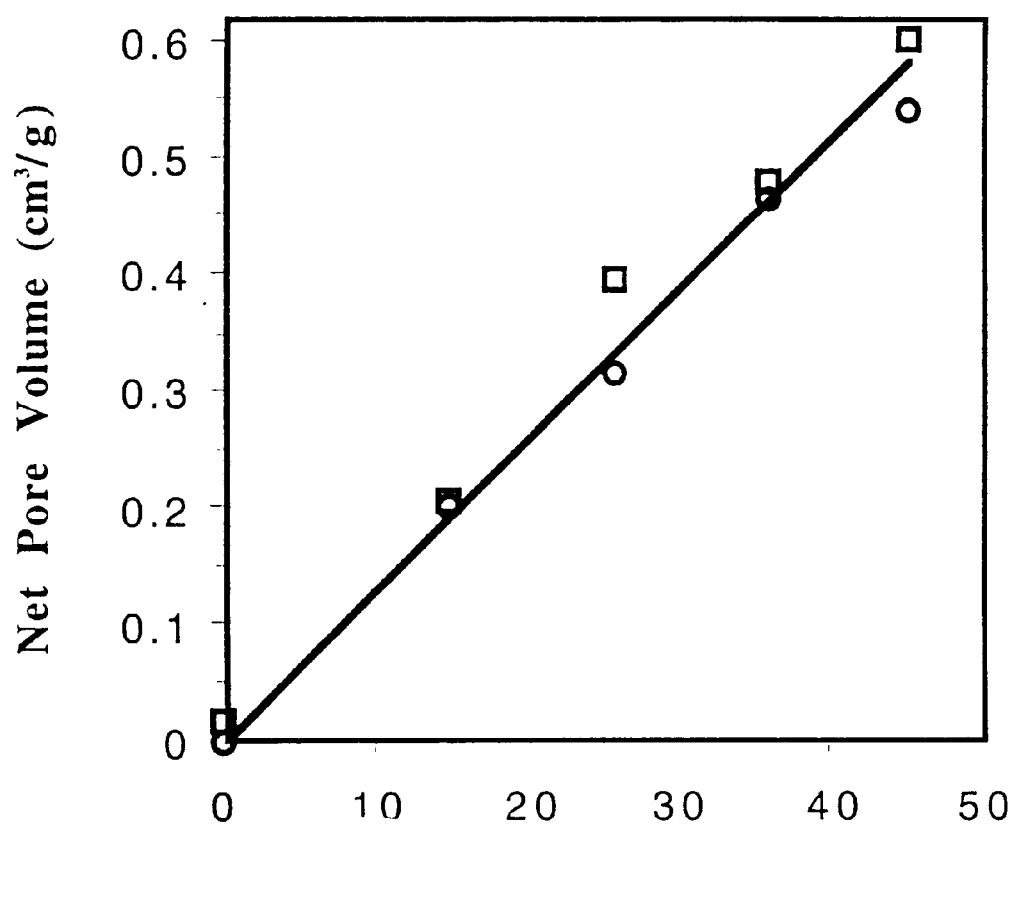
FIG. 4 is a graphical representation of the relationship between net pore volume and concentration of glucose after water extraction for the acid and base catalyzed samples of Example 1 (○) and Example 2 (□)

The pores or channels in the silica materials after removing D-glucose by extraction come from the space previously occupied by the pore forming molecules. In fact, analysis on the net pore volume and BET surface, which are the differences between the water-extracted and as-synthesized samples, reveals that they are linearly dependent on the D-glucose concentration up to 45 wt %, with good correlation coefficients of $R^2$=0.92 to 0.99 as shown in FIGS. 3 and 4. As such, the observed total surface areas and pore volumes in the extracted materials in Table 1 are mainly contributed from the internal voids.

The infrared spectra of both as-synthesized and water-extracted samples show the major absorption bands associated with network Si—O—Si vibrational modes at about 460, 790, 1080, and 1220 cm$^{-1}$, along with Si—OH asymmetrical stretching at about 960$^{-1}$ cm and SiO—H bond stretching at 3400 cm$^{-1}$. As anticipated, intensity of the band at 2940 cm$^{-1}$ for C—H stretching of the glucose component in the as-synthesized samples increases with glucose concentration. This band disappeared after water extraction, indicating the removal of the glucose pore forming material. The complete removal of glucose is further supported by the fact that the extracted samples showed little or no weight loss upon heating to 800° C. under air in the TGA measurements.

Since the irreversibility of the nitrogen isotherm as indicated by the hysteresis loop as demonstrated in FIGS. 1 and 2 is quite commonly observed in mesoporous materials, various reasons are asserted to be the cause of its origin and interpretation. Without wishing to be bound by theory, it may be attributed to network effects of interconnecting pores generated by the pore forming molecules such as glucose. The ink-bottle-shaped pore structure or pore size inhomogeneity may also lead to nitrogen isotherm with H2 hysteresis. In addition, it cannot be ruled out as a reason that the system may be incapable of reaching equilibrium during the acquisition of each data point. Lastly, it is also known that the meniscus of condensed nitrogen within the capillary pores becomes instable and leads to the steep region of the desorption branch at the lower closure point at P/P$_o$ of about 0.42. Although the inventors are unable to differentiate the contributions of these various factors with respect to the observed isotherms, network effect and ink-bottle shaped pore structure are considered the major factors for the occurrence of Type H2 hysteresis loops. In spite of the complexity and uncertainty in using gas adsorption to determine the pore size and distribution of mesoporous solids, this method still provides a good description of pore size distribution for a series of samples. The pore diameter values were determined by the BJH method and are listed in Table 1.

Figure 5:
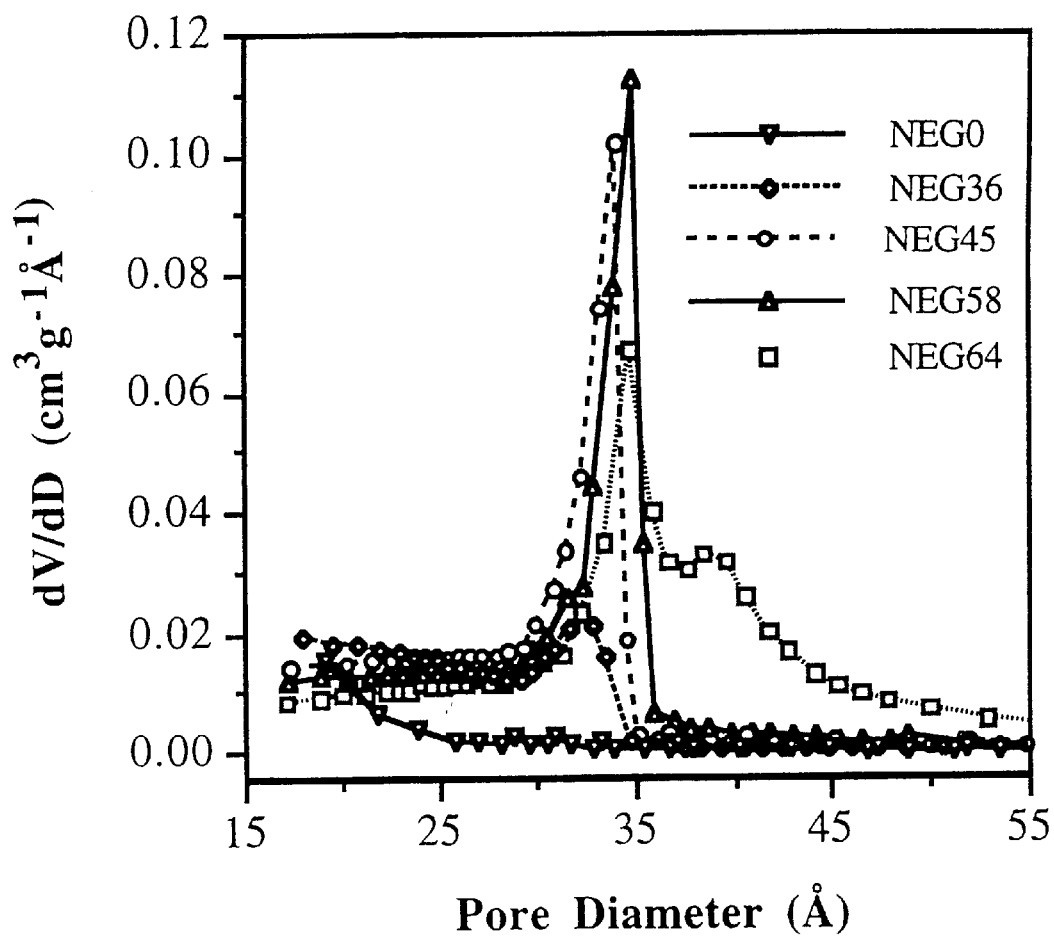
FIG. 5 is a graphical representation of BJH pore size distribution derived from nitrogen desorption isotherms which plots differential volume as a function of pore size for the silica matrices formed in Example 1.
Figure 6:
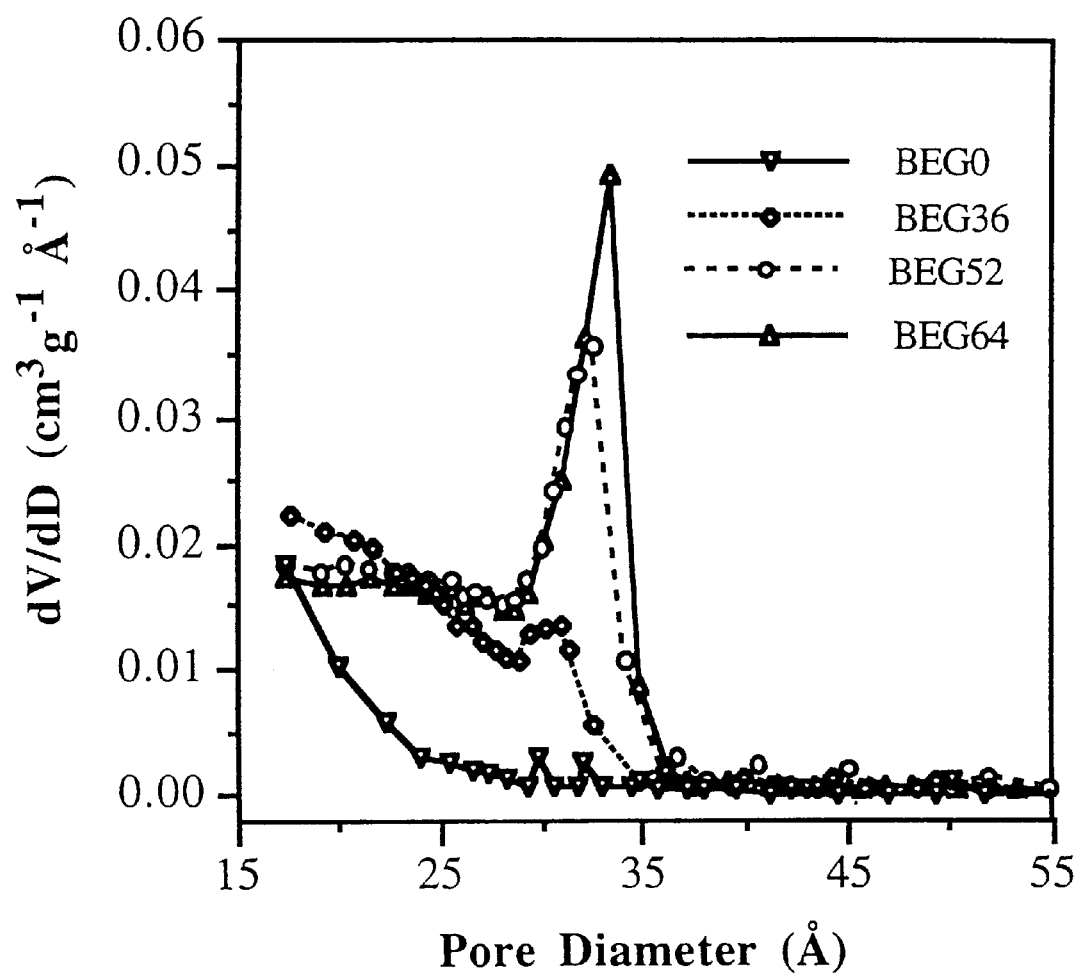
FIG. 6 is a graphical representation of BJH pore size distribution derived from nitrogen desorption isotherms which plots differential volume as a function of pore size for the silica matrices in Example 2.

FIGS. 5 and 6 show the BJH pore size distributions by plotting differential volume as a function of pore size for the silica matrices obtained from the desorption branches of the nitrogen sorption isotherms at −196° C. according to the BJH method with the Halsey equation for multilayer thickness. For glucose concentrations of 45–64 wt % in the sodium hydroxide systems (FIG. 5), or of 45–58 wt % in the sodium hydroxide-neutralized hydrochloric acid-catalyzed systems (FIG. 6), the extracted silica matrices possess narrowly distributed mesopores centered at about 3.2 or 3.5 nm, respectively. The BJH pore diameters in Table 1 are around 32 to 35 Å at the glucose concentrations of 45 wt % and higher. The BET average pore diameter, derived from V/S$_{BET}$, increases with glucose concentration. Pore size distributions from the adsorption branches of isotherms also show a similar pattern as in FIGS. 5 and 6 but with broader distributions. The pore volumes obtained at P/P$_o$ of about 1 and the mesopore surface areas calculated from the BJH method are found to increase with the glucose content. Both micropores and mesopores in the materials contribute to the observed pore volumes and areas, which could be differentiated approximately by t-plot analysis. As the glucose content increases, the contribution from the micropores decreases. At the glucose content of 36 wt % or higher, the contribution from mesopores become dominant while that from the micropores is negligible. All these results are quite similar to those obtained in the acid-catalyzed system. The pattern of nitrogen sorption isotherms closely resemble those of mesoporous materials formed using polymeric ethylene oxide neutral surfactants. The materials exhibit numerous cylindrically-shaped interconnecting networks of pores.

Without wishing to be bound by theory, the inventors believe that the non-surfactant pathway of the pore forming materials in the mesostructures of the materials of the invention are governed by several factors which affect generation of mesoporous structures without causing macroscopic phase separation in a certain composition range. The pore forming materials of the invention are generally compounds having high affinity for intermediate materials derived from the organosilicon material in the sol-gel matrix, and include the appropriate hydrophilicity and solubility with low volatility. Further, since the pore forming molecules were used in relatively high concentrations and the pore diameters achieved were greater than the size of the individual pore forming molecules, the pore forming molecules are likely present in forms of aggregates whose interactions with the inorganic material in the matrix through hydrogen bonding play an important role in directing mesoporous formation prior to and/or during gelation.

The hydrogen bonding between the organic pore forming material and the intermediates of the inorganic species, e.g., Si(OR)$_{4-x}$(OH)$_x$, brings the two major components together and forms a homogeneous sol without macroscopic particulation of inorganic species. It may also facilitate the hydrolysis and further condensation of the —OH functional inorganic intermediate species, e.g. silanol groups. The sols in the above Examples underwent gelation faster at higher concentrations of D-glucose which suggests the presence of D-glucose promoting condensation. After gelation and during subsequent drying, the affinity of the pore forming material for the intermediate species, together with the high and increasing viscosity of the system, might keep the inorganic and organic moieties from macroscopic phase separation, while the volatile solvent molecules and reaction by-products, such as alcohol and water, were gradually evaporated from the system. The interactions between the intermediates and the pore forming molecules would stabilize the silicon-based framework and prevent it from fracturing caused by capillary pressure and internal stress build-up during drying. As a result, an organic-inorganic composite mesoporous material with bicontinuous networks of silica and the pore forming material were obtained as transparent, monolithic solids, and the removal of the pore forming material provided silica materials with interconnecting mesopores.

The above Examples demonstrate that the resulting mesoporous materials formed using the invention include high specific surface areas, pore volumes and narrow pore distributions with BJH pore diameters of 3.2 to 3.5 nm, indicating mesoporosity. The pore parameters generally increase and the nitrogen sorption isotherms gradually transform from Type I to Type IV with H2 hysteresis as the glucose concentration increases in synthesis. As concentrations of <36 wt % glucose, both micropores and mesopores contribute to porosity, and at levels of 36 to 64 wt % glucose, mesopores are dominant with narrow pore size distributions.

EXAMPLE 3

In this Example, acid phosphatase is immobilized in a mesoporous material. Acid phosphatase (ACP, EC 3.1.3.2, Type I from wheat germ, 0.4 units/mg, lot 37H7025) and magnesium chloride were purchased from Sigma, St. Louis, Mo. Tetramethylorthosilicate and p-nitrophenyl phosphate disodium salt hexahydrate (PNPP) were supplied by Aldrich, Milwaukee, Wis. Methyl alcohol, D-glucose, sodium hydroxide and hydrochloric acid were from Fisher Scientific, Fair Lawn, N.J. In addition, p-nitrophenol was purchased from Acros Organic in New Jersey. All chemicals were used as received.

A homogeneous mixture of 5.0 ml tetramethylorthosilicate, 6.0 ml of methanol, 15 $\mu$l of 40 mmol hydrochloric acid and 0.7 ml of water was formed in a beaker. Varied amounts of 50 wt % D-glucose aqueous solution were added under agitation at room temperature, followed by addition of 10 mg of ACP (in a 1.0 ml water solution) upon cooling the mixture to 0° C. The mixture was sealed in the beaker with a piece of plastic film and allowed to reach room temperature under moderate magnetic stirring. Upon gelation, within a few hours at room temperature, the film was pierced with 12–15 holes using a hypodermic syringe needle to allow the evaporation of solvents. After one day, the sample-containing beaker was removed from a fume hood and put into a vacuum oven and dried to react constant weight at room temperature in about six days. Transparent or opaque samples of weights ranging from 2.4 to 5.5 g depending on the concentration of D-glucose in the biogels (from 0–60 wt %) were obtained. The samples were crushed with a mortar and pestle into fine powder (10–100 $\mu$m) and kept in sealed vials in a −15 ° C. freezer ready for enzymatic activity assay or other property evaluation.

The general procedures for the enzymatic activity assay of ACP in solution and in immobilized form were carried out using standard methods. Assay of ACP activity was determined from hydrolysis of pNPP by following the absorbence increase at 405 nm for the alkalinized solution owing to liberation of phenolate ion. Generally, the assay system (16 ml) consisted of 0.06 units of free (ACP Free) or immobilized ACP (Samples AMAC0–AMAC60), and the assay solution included magnesium chloride (1 mmol), pNPP (0.02–5.0 mmol), and sodium citrate/citric acid buffer (50 mmol with pH 4.0–6.2). The assay procedure included weighing a certain amount of the immobilized ACP sample powder (30–80 mg) containing nominally 0.06 units of ACP into a test tube. For the ACP-free silica glass control (AMAC Control), 50 mg of powder was used. Then 15 ml of water was transferred into the sample-containing tube and shaken often at room temperature.

After one hour, the sample was centrifuged for 2–3 minutes to ensure the complete settling of the sample powder at the bottom of the tube. Then, the supernatant was carefully decanted by inverting the tube, and absorbing the last droplet of liquid at the trim of the tube using a sheet of tissue paper if necessary. The washing procedures were repeated two more times at one hour intervals to ensure removal of glucose and any free enzyme which was not trapped. Then magnesium chloride and buffer solutions were pipetted along with water, if required for dilution, into the sample tube and were shaken well. After 30 minutes of activation and equilibrium, the substrate pNPP solution was pipetted into the tube and timed. The mixture was shaken often. At certain time intervals, 0.5 ml of supernatant were withdrawn from the assay system immediately after centrifugation and mixed with 5 ml of sodium hydroxide (1N) solution. Immediately after mixing, the concentration of p-nitrophenol in the alkaljnized solution was evaluated by measuring absorbance at 405 nm on a spectrophotometer that was calibrated with p-nitrophenol solutions in 1N sodium hydroxide. The apparent enzyme activity of ACP was characterized by the rate of generation of p-nitrophenol, expressed in $\mu$mol/min.-mg of ACP in the assay system. The activity of free ACP in solution was estimated directly by using its aqueous solution as the enzyme source. The specific activity was calculated from the kinetic assay data by linear regression method. Fixed-time assay was also used to estimate the enzymatic activity by taking the readings of absorbance at the start and the end of the reaction. There was no significant difference in activity measured from the two assay methods. Both kinetic assay and fixed-time assay methods were used.

The estimation of activity remaining of ACP upon immobilization in silica gel was carried out at the optimal pH for ACP, i.e., pH of 5.0, in a 50 mmol citrate buffer with a substrate concentration [PNPP]=2.0 mmol at room temperature. The percentage activity remaining was obtained by comparing the specific activity of the immobilized enzyme with that of free ACP assayed under the same conditions.

The determination of the reaction kinetics of the free and immobilized enzyme was carried out in a pH 6.2 citrate buffer. During the assay, 0.06 units of ACP were mixed with the assay solution containing from 0.02 to 5.0 mmol of the substrate, pNPP.

The pH profiles for both free and immobilized ACP were conducted at room temperature using a substrate concentration of [pNPP]=2.0 mmol. A 50 mmol citrate buffer in the pH range of 4.0–5.9 was used.

In evaluating thermal stability, the immobilized ACP was first washed with water (3×10 ml), and then mixed with the assay mixture (pH 6.2) without adding pNPP. Free ACP was dissolved in the same solution. The sample-containing tube was sealed with plastic film and put into a water bath preset at a certain temperature, such as 23, 50 or 70° C., for one hour. The tube was then taken out and allowed to cool in air to room temperature, followed by assay of activity remaining at [PNPP]=5.0 mmol initiated by adding pNPP.

For room temperature storage stability, the sample powder from the as-synthesized biogels was sealed in a vial with a cap and put aside. After 70 days, the sample was estimated for activity remaining at a pH of 6.2 and [PNPP]=5.0 mmol by following the general assay procedure.

In order to evaluate any possible leaching of ACP from the mesoporous materials during the assay, part of the supernatant was separated from the sample powder by centrifugation and decantation when the activity assay was completed. The absorbance change after alkalinzing the supernatant with sodium hydroxide with time was subsequently monitored and compared to that of a blank control to determine any enzymatic activity.

The characterization of the microstructure parameters, for example, pore size and distribution, specific surface area and pore volume of the mesoporous matrix was carried out on a Micromeritics 2010 system using procedures as described in Examples 1 and 2. The powder sample (from 0.2–0.3 g) was extracted with water (9×10 ml) at room temperature for 3 days before the measurement. After water extraction, the sample was first dried in a 115° C. oven and then degassed at 200° C. and $10^{-6}$ torr overnight prior to nitrogen adsorption-desorption measurement at −196° C. The pore parameters were calculated using the Micromeritics software.

The weight percentage of D-glucose in dry biogel sample was determined from the weight loss in air at 750° C. at which glucose decomposed completely. The sample was first dried in a 110° C. oven overnight, and then heated to 750° C. at a heating rate of 10° C./minute in a muffle furnace.

The effect of glucose concentration on immobilized ACP activity was determined as follows. The apparent specific enzyme activities, were determined as noted above for all samples and appear in $\mu$mol/min.-mg of ACP for the immobilized and free ACP determined at pH 5.0 and [pNPP]=2.0 mmol at room temperature and are sunmarized in Table 2. The catalytic activities of the entrapped ACP as well as the free ACP are larger at pH 5.0 than at higher or lower pH. This is in agreement with the optimal pH 5.0 previously reported for ACP obtained from wheat germ.

At optimal pH 5.0, the entrapped ACP retained from 7% to 22 % of the free enzyme activity which was estimated to be 0.596 $\mu$mol/min-mg under the same conditions. At other pH values, the immobilized ACP had similar percentage activity remaining when compared to the free ACP activity, as will be discussed also with respect to the pH profile. The enzymatic activities for the immobilized samples were found to be dependent on the concentration of D-glucose used in the preparation of the biogels. That is, when 36 wt % or less glucose was added, the resultant gels did not exhibit remarkably improved enzymatic activities in comparison with the glucose-free sample. But, at 42 wt % or more glucose, the gels demonstrated higher activity than the glucose-free sample, increasing with the amount of glucose (Table 2). When 60 wt % of glucose was used, the sample exhibited almost three-fold activity over the glucose-free sample, which is about 22 % of the free ACP activity. The difference in apparent catalytic activity for the entrapped ACP samples was associated with the biogel microstructure.

Figure 7:
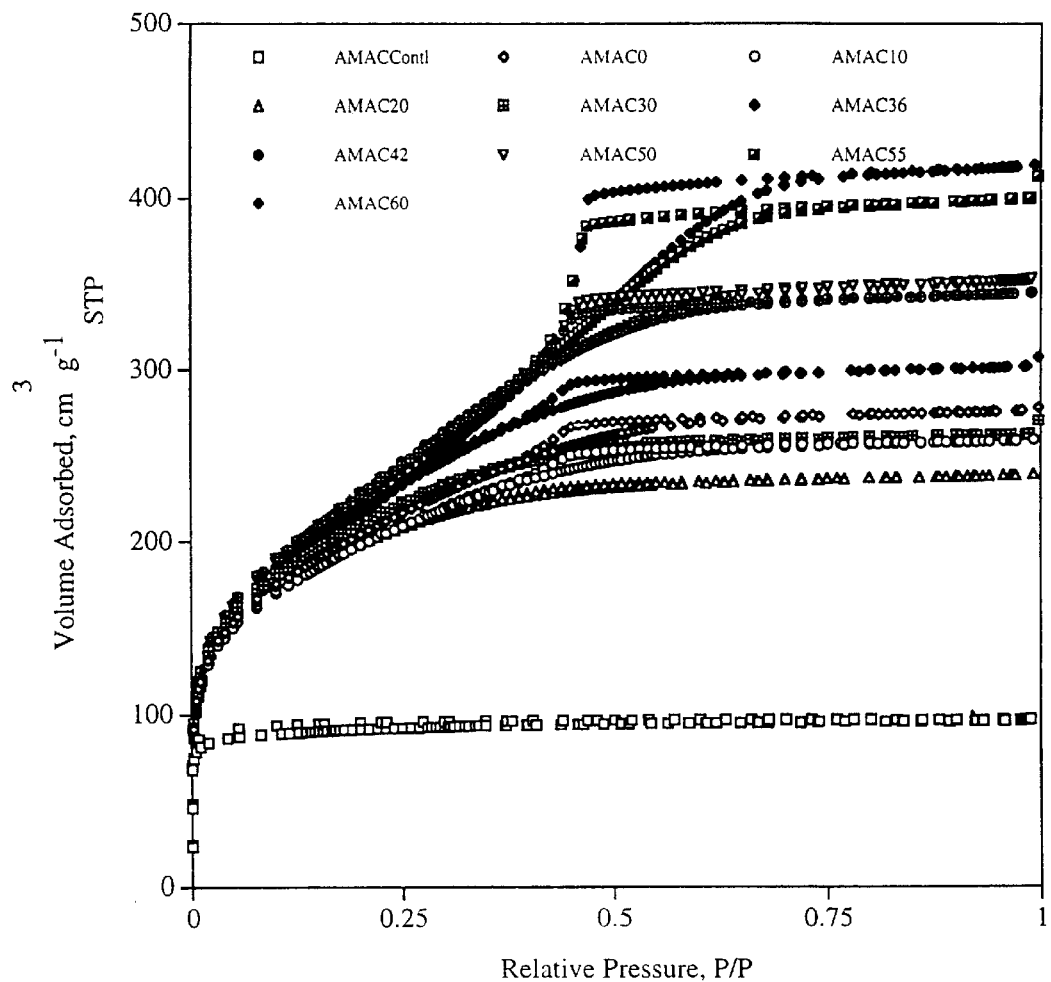
FIG. 7 is a graphical representation of the nitrogen adsorption-desorption isotherms at −196° C. for samples after water extraction in Example 3.

For the glucose-containing samples, their enzymatic activities were associated with the concentration of D-glucose used in the formulation of the bioactive gels. The matrix pore structure parameters, e.g., the specific surface area and pore volume as well as pore size and distribution, were also dependent on the concentration of glucose present in the gels in accord with Examples 1 and 2. As such, a relationship appeared to exist between the concentration of glucose, the apparent enzymatic activity of the gels, and the pore structure parameters of the host matrix. The pore parameters of the silica matrix, obtained by removing D-glucose from the as-synthesized materials via solvent extraction, revealed further information about the biogel microstructure. The pore structure parameters of the silica matrices, obtained from nitrogen sorption isotherms, are also summarized in Table 2. The nitrogen sorption isotherms at −196° C. (FIG. 7) show that when neither D-glucose nor ACP is added, the resultant matrix exhibits a Type I isotherm and is essentially a microporous silica, similar to the conventional xerogels prepared in the presence of acid catalyst. When ACP (5 mg ACP/gram of $SiO_2$) was present in the biogels without adding glucose (the glucose-free sample), micropores and mesopores coexisted in the corresponding product, as evidenced by the t plot. When both ACP and glucose were used to formulate the composite biogels, the nitrogen sorption isotherms for the matrices shifted from Type I to Type IV with increasing irreversibility as indicated by the growing size of hysteresis loops while the concentration of D-glucose increased.

When 36 wt % or less glucose was used, the resultant matrices had smaller pore volumes and pore diameters than the glucose-free sample, but had comparable BET surface areas, similar to the results of Examples 1 and 2. The matrices made with more than 42 wt % of glucose had larger pore volumes and pore diameters than the glucose-free sample and increased with glucose concentration (Table 2). It is noted that at high pore,forming material concentrations, the BJH surface areas, reflecting mesopores>17, also increased with glucose concentration, while the BET surface areas remained about the same.

Figure 8:
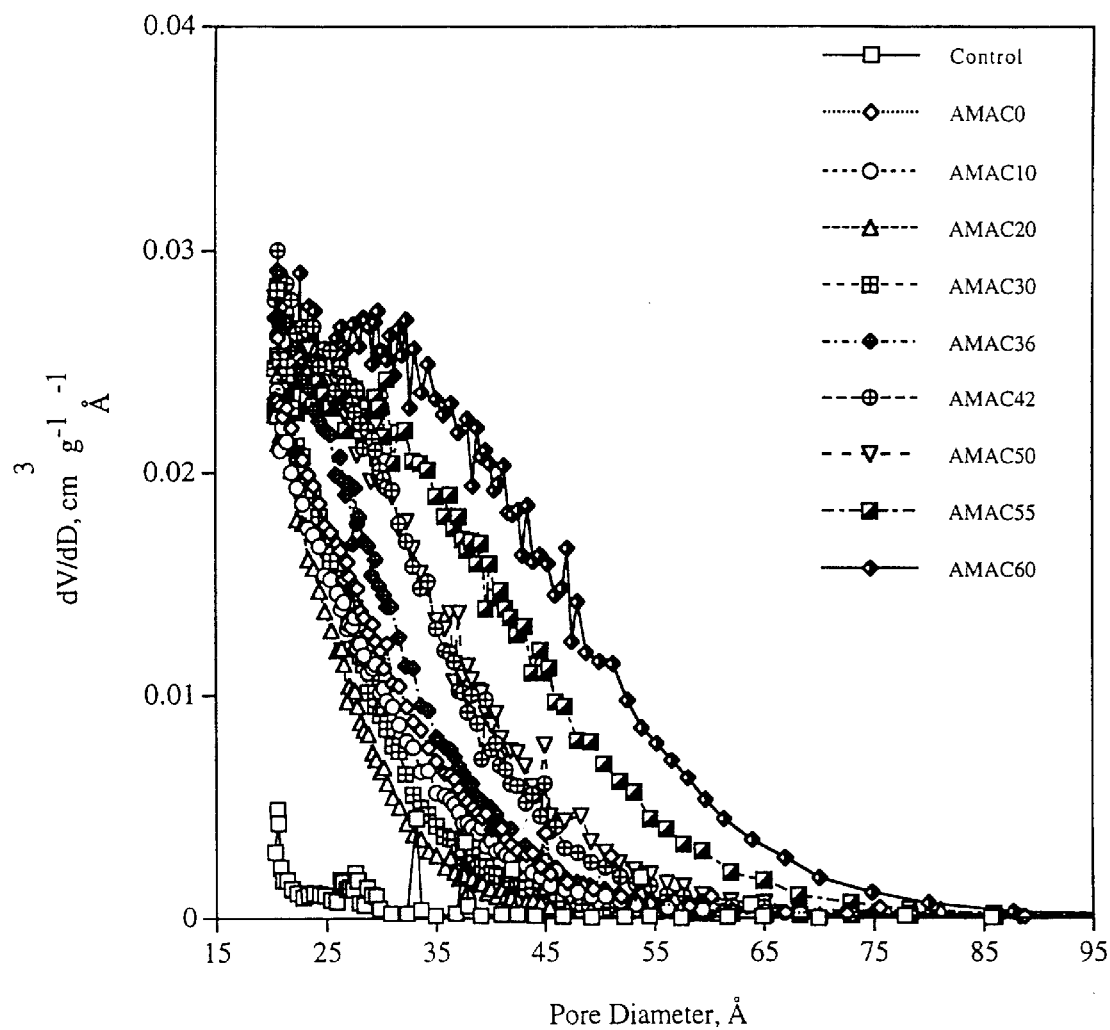
FIG. 8 is a graphical representation of the BJH pore size distributions derived from nitrogen adsorption branches at −196° C. for samples after removal of D-glucose with water extraction as in Example 3.
Figure 9:
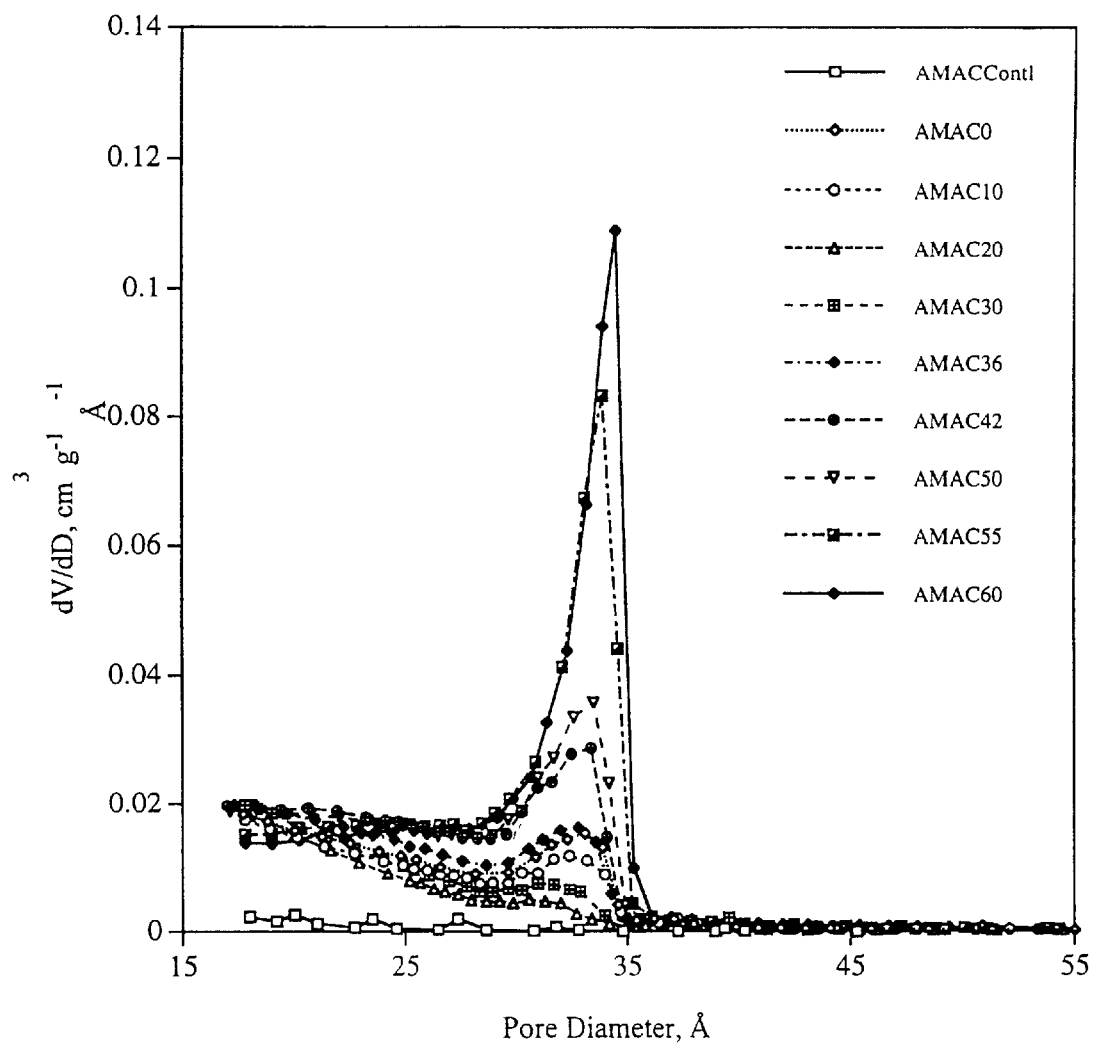
FIG. 9 is a graphical representation of the BJH pore size distributions derived from nitrogen desorption branches for samples after removal of D-glucose with water extraction as in Example 3.

FIGS. 8 and 9 show, respectively, the BJH adsorption and desorption pore size distributions of the biogel matrices. The individual pore size distribution curve was obtained from the adsorption or desorption branch of the nitrogen sorption isotherms by plotting differential volume as a function of pore size. It is noted that the pore size distribution for a certain sample derived from the nitrogen adsorption branch was broader than that from the desorption branch, and the corresponding average pore diameter was also greater when calculated from adsorption isotherm than that from the desorption branch. The irreversibility of the nitrogen isotherms may be attributable to the existence of ink-bottle pores and interconnecting pore network structure in the silica matrices prepared using this pore forming material as described above. For the Type IV isotherm, the BJH adsorption pore size distributions may reflect the cavity size distributions, while the desorption pore size distributions may correspond to the throat size distributions. If this is the case, then FIGS. 8 and 9 demonstrate that both cavity and throat sizes increase with D-glucose concentration when glucose is 20 wt % or higher in the biogels. When D-glucose accounts for 42–60 wt % of the biogels, the extracted silica matrices possess narrowly distributed pore openings centered at 32.5 to 34.5 Å.

Figure 10A:
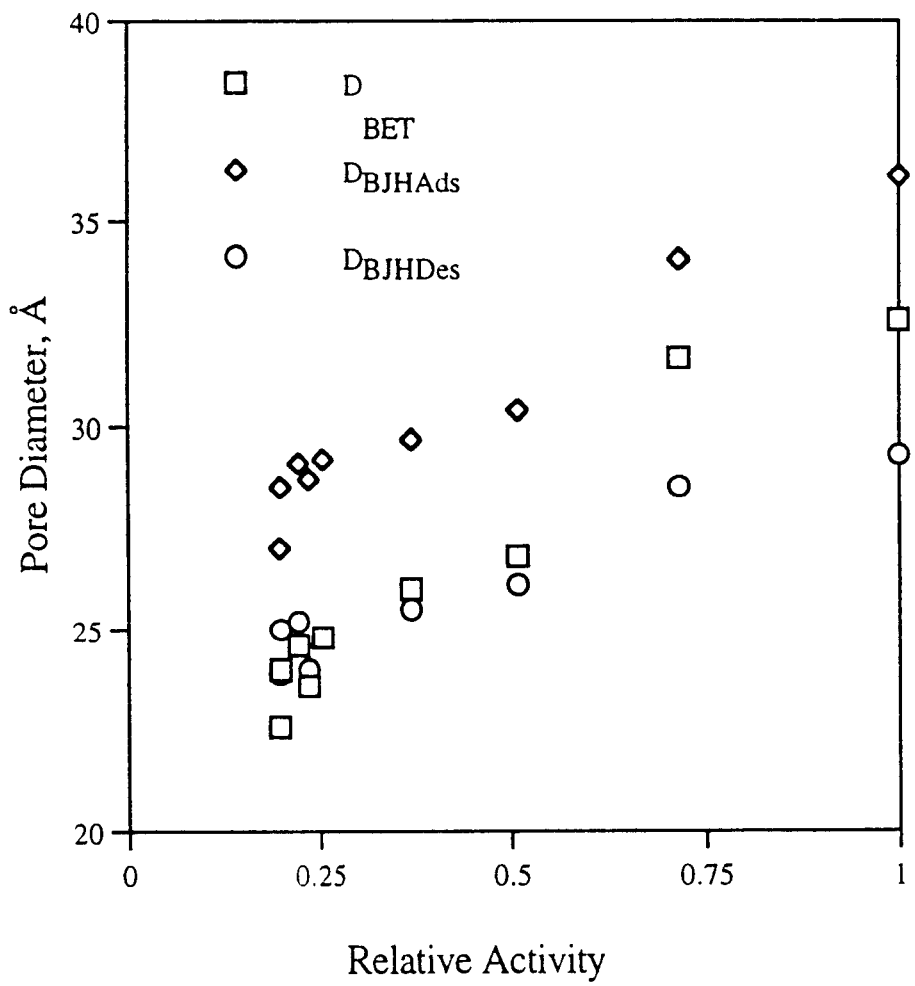
FIG. 10a is a graphical representation of the relationship between matrix pore diameter and relative enzymatic activity of immobilized ACP as in Example 3.
Figure 10B:
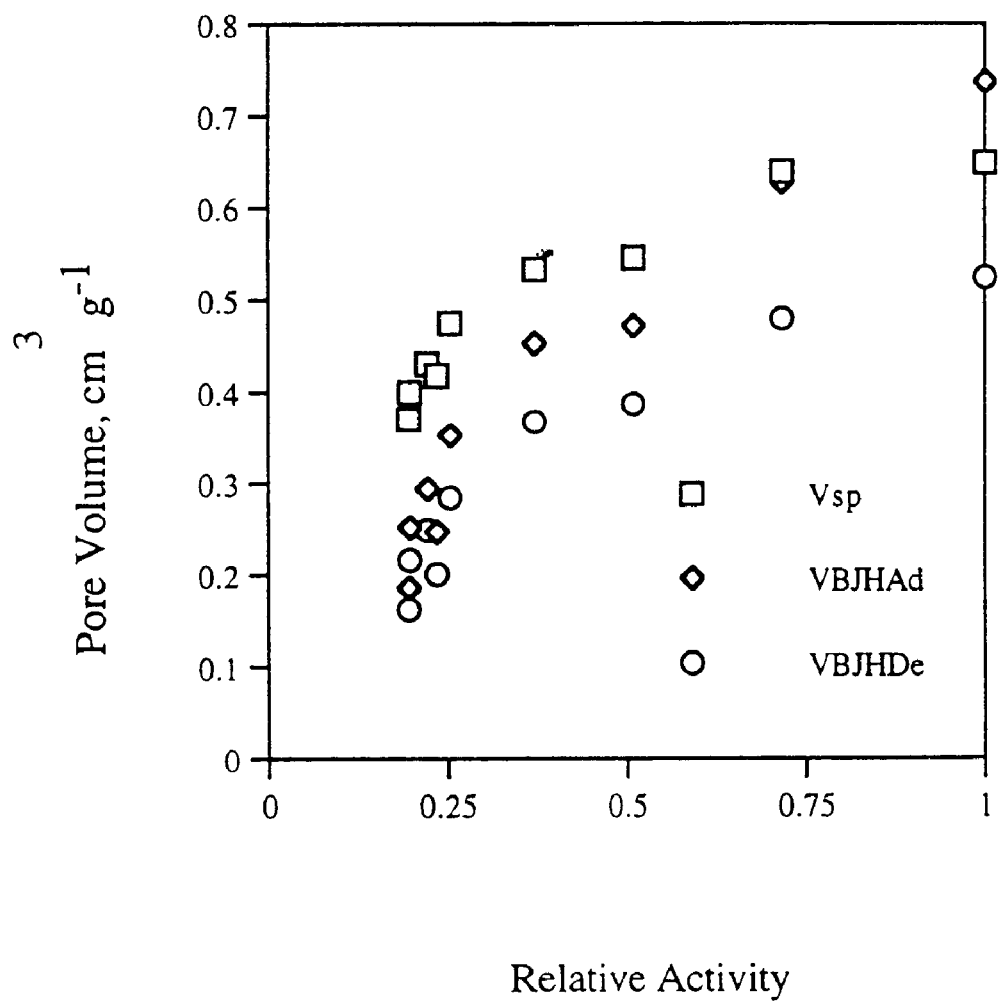
FIG. 10b is a graphical representation of the relationship between matrix pore volume and relative enzymatic activity of immobilized ACP as in Example 3.

Analysis of the experimental data on immobilized ACP activities and the pore structure parameters of the matrices revealed that the apparent enzymatic activities were closely associated with the pore volumes and diameters of the host matrices. There was moderate to strong linear relationship between the average apparent activity and the pore diameters or pore volumes with correlation coefficients of $R^2$=0.86–0.95, as shown in FIGS. 10a and 10b. The average enzymatic activity for each sample was calculated from the activity data in the range of pH 4.0–6.2 and [pNPP]=0.5–5.0 mmol/L. Without wishing to be bound by theory, the inventors believe that large pore diameter and volume contribute to the formation of a favorable microenvironment for the entrapped enzyme inside the matrix pores in which the chemical and physical properties are similar to the bulk solution due to ease of mass transfer of chemicals and ample space in the vicinity of the enzyme active site. In contrast, when ACP is present in the relatively small pores, it would have a surrounding much different from the external bulk solution.

The BET surface area, in the range of 650–820 m²/g for the ACP-containing samples, does not seem to be a significant factor affecting the rate in the immobilized enzyme-catalyzed reaction as in the conventional chemical reactions using heterogeneous catalysts. This may be attributable to the difference in the active sites of these two kinds of catalysts. It is generally accepted that active sites on the surface are important for framework-confmed catalysts which require large areas exposed to and attainable by reactants for an effective reaction. But for the enzyme-catalyzed reactions, it seems that the transfer of mass from the bulk solution to the active site of the immobilized enzyme is critical. Therefore, the pore diameter and pore volume of the carrier, instead of its BET surface area, are the more important factors affecting the overall catalytic activity of a highly active enzyme.

numerous channels and provides ample space around the entrapped enzyme macromolecules to accommodate the chemicals from the bulk solution. The degree of freedom for the migration of chemicals inside the glucose-formed matrix would be greater than within the glucose-free sample. However, the channels or pore sizes of the silica matrix shall be adjusted so as to facilitate the penetration of small molecules such as substrate but not to allow the leakage of the entrapped enzyme macromolecules to the bulk solution.

Figure 11A:
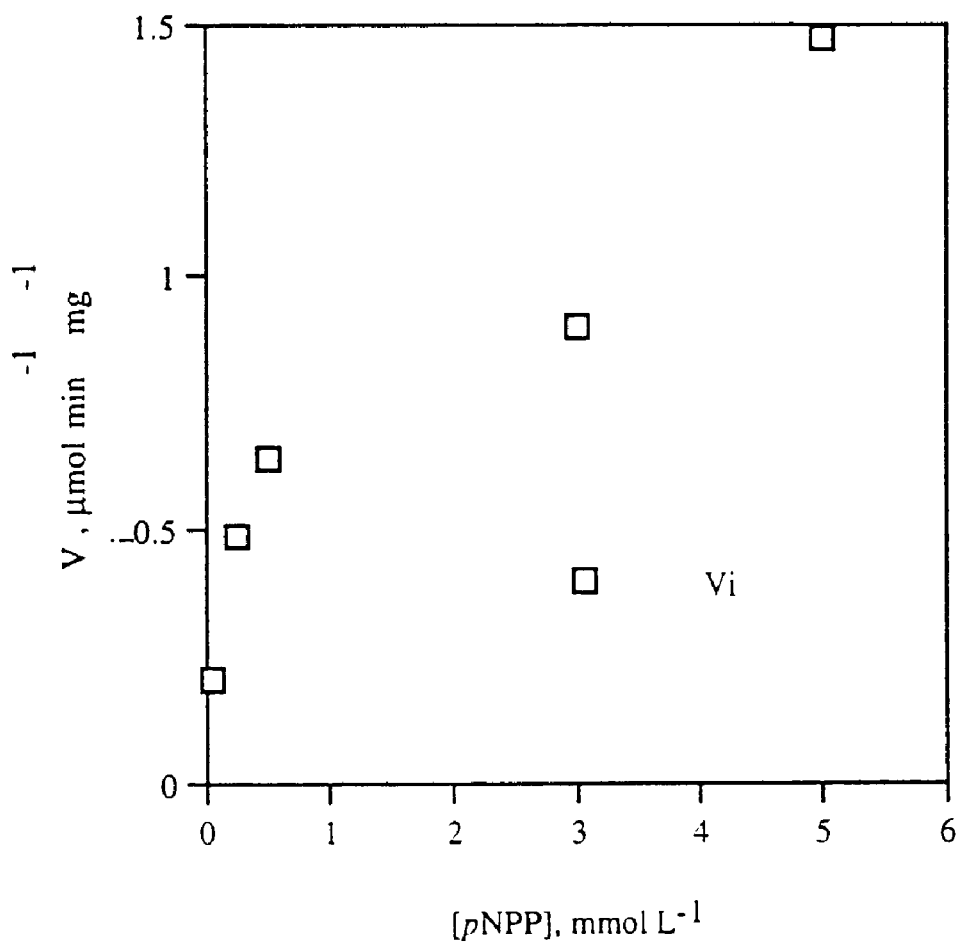
FIG. 11a is a graphical representation of the relationship between enzymatic activity of free ACP and the concentration of pNPP at pH 6.2 and room temperature as in Example 3.

The effect of the substrate pNPP concentration on the reaction kinetics of free and immobilized ACP was investigated to further discern if the immobilized enzyme-catalyzed reaction was pore-diffusion controlled, kinetically controlled, or a combination of both. In this study, the assay mixture consisted of pNPP in the range of 0.02 to 5.0 mmol/L in a pH 6.2 citrate buffer. The plot of specific enzyme activity vs. [pNPP] for free and several immobilized ACP samples synthesized in the presence of high concentrations of glucose (50, 55, and 60 wt % respectively), are demonstrated in FIGS. 11a and 11d. For free ACP, the various derived forms of the Michealis-Menten equation,

TABLE 2

| Sample | D-glucose Content (Wt %) Calc | D-glucose Content (Wt %) Found | Enz. Activity (μmol/min.-mg) | $S_{BET}$ (cm²/g) | V (cm³/g) | BET Pore Dia. (Å) | BJH Pore Diam. (Å) | Micropore Area (cm²/g) | Micropore Vol. (cm³/g) |
|---|---|---|---|---|---|---|---|---|---|
| AMAC Control | 0 | 12.2 | 0 | 264.7 | 0.1500 | 22.7 | <17 | 218.2 | 0.1210 |
| AMAC0 | 0 | 10.0 | 0.046 | — | 0.4300 | 24.6 | 33.1$_{(s)}$ | 82.9 | 0.0450 |
| AMAC10 | 10 | 17.5 | 0.044 | 667.3 | 0.4000 | 24.0 | <17 | 110.5 | 0.0613 |
| AMAC20 | 20 | 23.4 | 0.054 | 653.3 | 0.3696 | 22.6 | <17 | 157.0 | 0.0884 |
| AMAC30 | 30 | 32.7 | 0.055 | 706.7 | 0.4178 | 23.6 | <17 | 109.7 | 0.0619 |
| AMAC36 | 36 | 38.9 | 0.050 | 765.6 | 0.4750 | 24.8 | 32.8 | 34.8 | 0.0169 |
| AMAC42 | 42 | 43.6 | 0.060 | 821.8 | 0.5335 | 26.0 | 32.5 | — | — |
| AMAC50 | 50 | 49.1 | 0.079 | 814.2 | 0.5457 | 26.8 | 32.6 | — | — |
| AMAC55 | 55 | 54.6 | 0.101 | 805.6 | 0.6390 | 31.7 | 33.9 | — | — |
| AMAC60 | 60 | 59.3 | 0.130 | 796.2 | 0.6490 | 32.6 | 34.5 | — | — |

Figure 11B:
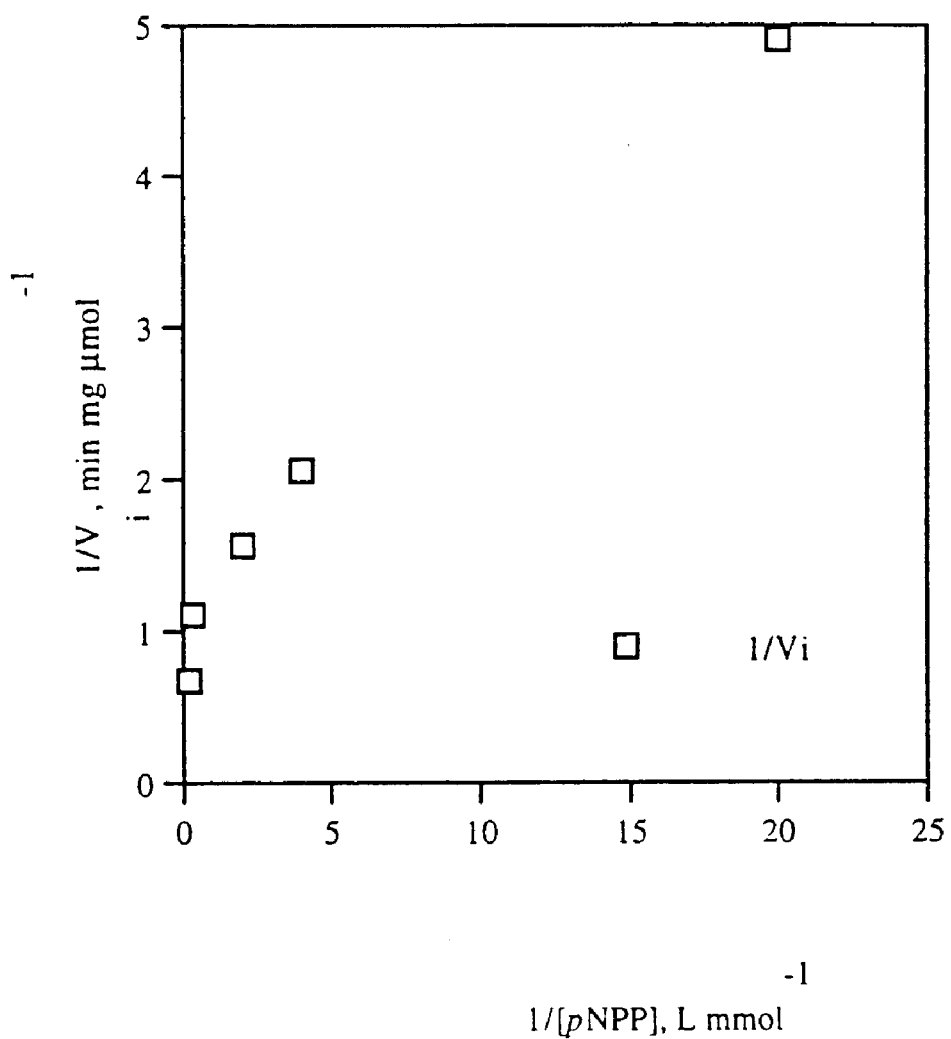
FIG. 11b is a graphical representation of the Lineweaver-Burk plot of free ACP at pH 6.2 and room temperature as in Example 3.
Figure 11C:
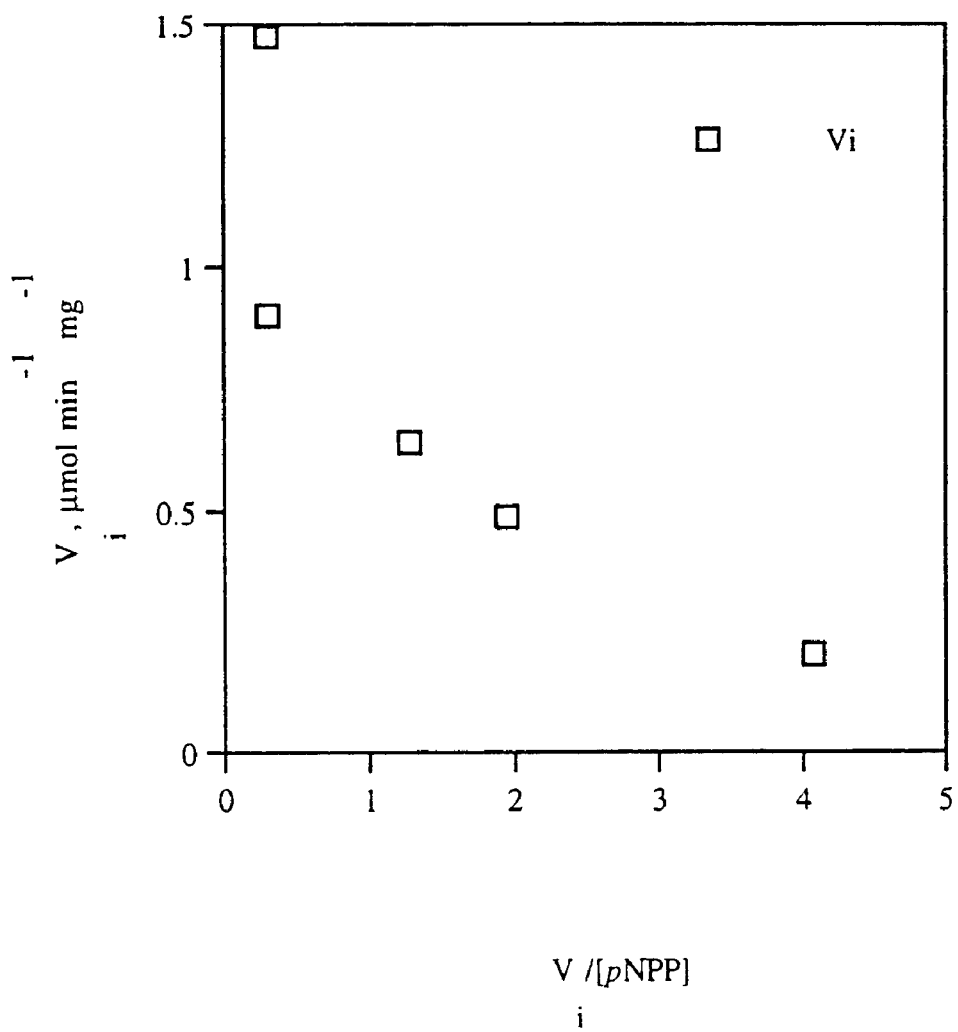
FIG. 11c is a graphical representation of the Eadie-Hofstee plot of free ACP at pH 6.2 and room temperature as in Example 3.

This Example demonstrates the direct immobilization of the enzyme molecules in mesoporous silica glasses through use of the neutral organic pore forming materials in accordance with the invention. During the formation of the biologically active composites comprising enzyme macromolecules, low-molecule-weight organic compound and highly crosslinked silica networks, the aggregation or assembly of the aggregates of the pore forming molecules and the hydrogen bonding between the intermediate silicate species and the pore forming molecules are believed to direct the formation of the nanophases in the hybrid materials as discussed above. The enzyme macromolecules, only comprising 0.5 wt % of silica though, may play a similar role. When glucose and ACP were introduced into the hydrolyzed tetramethylorthosilicate sol, the organic molecules interacted with the intermediate silicates via hydrogen bonding and the assembly of the organic molecules or the aggregates of the organic molecules likely participate and direct the formation of the hybrid phases. Without wishing to be bound by theory, it is expected that in as-prepared biogels, D-glucose and ACP are intermingled with silica networks. Upon completion of the enzyme immobilization process, both glucose and ACP became automatically part of the composite structure. Removal of D-glucose from the biogel prior to activity assay by extraction with water due to concentration gradients results in and expands such as Lineweaver-Burk, Eadie-Hofstee or Hanes-Woolf plot, may be used to construct the enzyme activity versus the substrate concentration graphs and to estimate the maximum velocity ($V_{max}$) and Michealis constant ($K_m$) under the assay condition used. For the dissolved ACP at pH 6.2, a downward bending in the double-reciprocal Lineweaver-Burk plot at [pNPP]=5 mmol was observed as shown in FIG. 11b which was probably due to the phenomenon of substrate activation at high substrate concentration. For the free ACP at pH 6.2 and room temperature, $V_{max}$ and $K_m$ derived from the Lineweaver-Burk plot are 0.86 μmol/min-mg and 0.16 mmol, respectively, which are close to that from the Eadie-Hofstee plot shown in FIG. 11c ($V_{max}$=0.90 μmol/min-mg and $K_m$=0.18 mmol) and smaller than that from the Hanes-Woolf plot ($V_{max}$=0.97 μmol/min-mg and $K_m$=0.23 mmol).

Figure 11D:
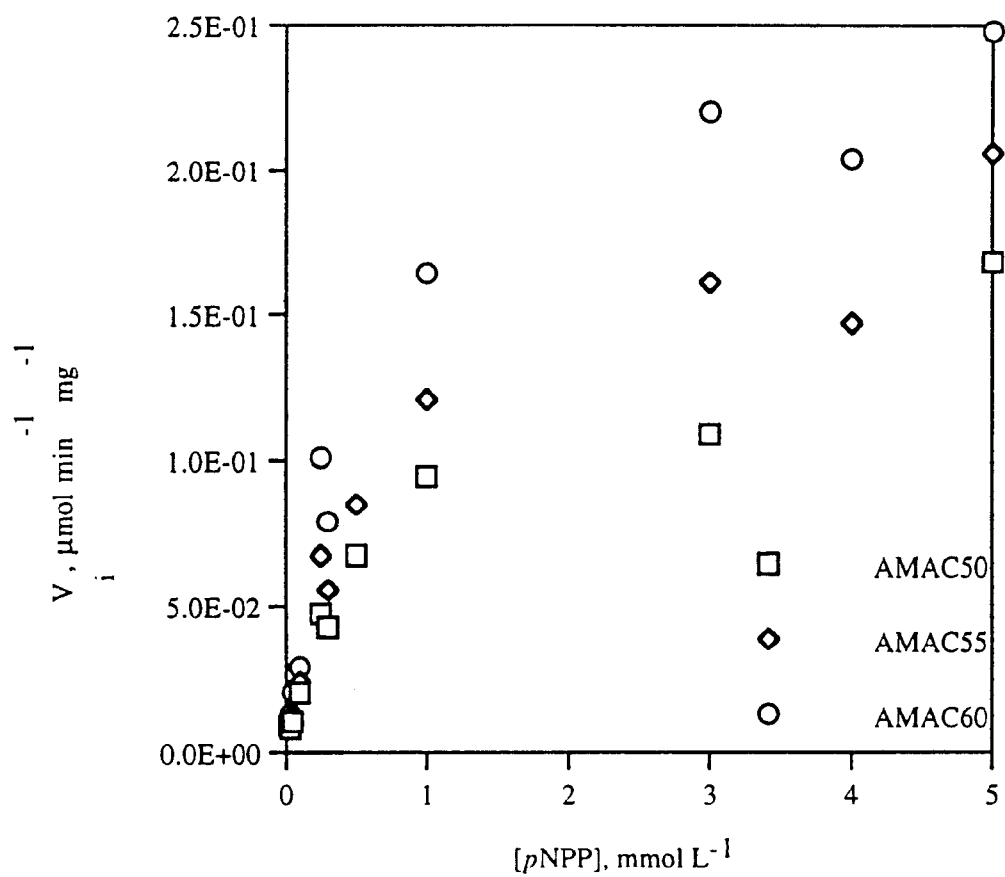
FIG. 11d is a graphical representation of the relationship between enzymatic activity of immobilized ACP at various D-glucose concentrations and the concentration of pNPP as in Example 3.
Figure 11E:
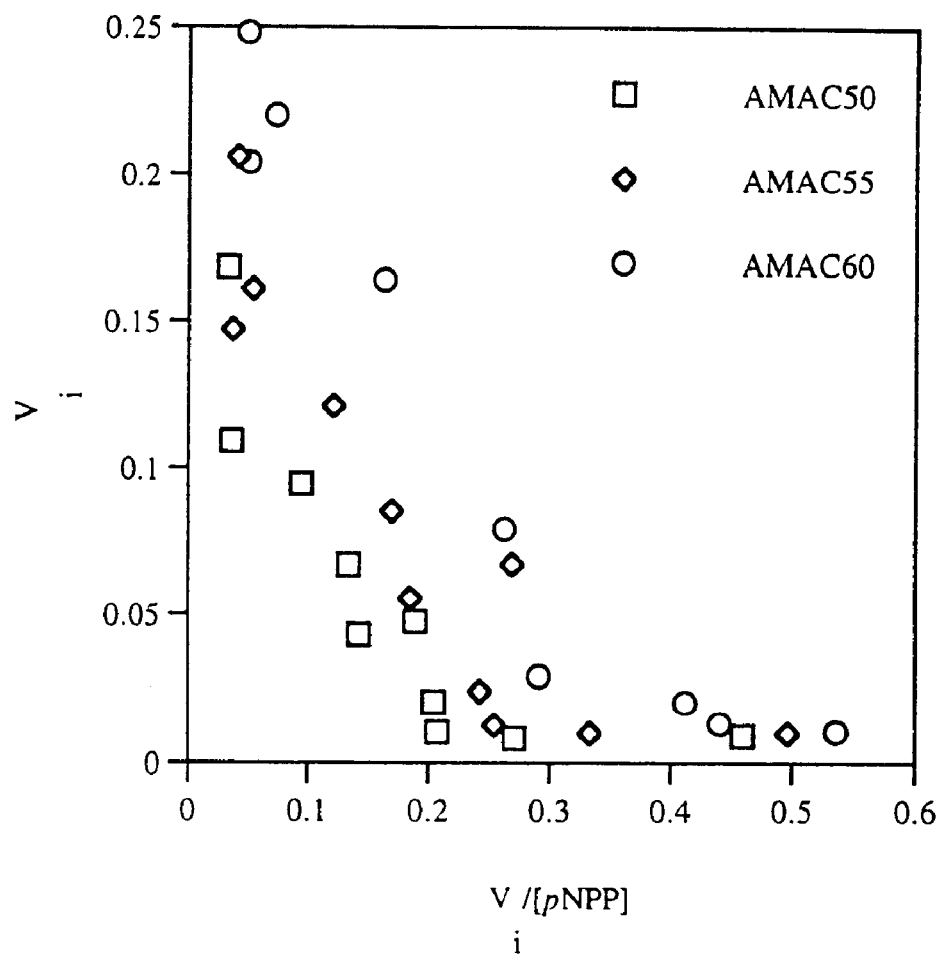
FIG. 11e is a graphical representation of the Eadie-Hofstee plots of immobilized ACP at various D-glucose concentrations assayed at pH 6.2 and room temperature as in Example 3.

For immobilized ACP samples, similar Lineweaver-Burk plots may be constructed. However, due to the complexity in the characterization and evaluation of the reaction kinetics of a heterogeneous biocatalyst owing to diffusional limitations, the Lineweaver-Burk plots were not linear in the whole concentration range for all the immobilized samples and appreciable deviation of the kinetic data from the linearity of the reciprocal plots was observed, by showing a concavity with respect to the abscissa, as shown in FIG. 11d. The curvature regime increased with decreasing pore size, indicating increasing internal transport resistances when the channel sizes is decreasing, as generally expected. The apparent $V_{max}$ and $K_m$ values, derived from the Lineweaver-Burk plots by linear regression of the data, were 0.017 μmol/min-mg and 0.75 mmol, 0.023 μmol/min-mg and 0.85 mmol, and 0.030 μmol/min-mg and 0.91 mmol, respectively, for the immobilized ACP samples made with 50, 55, and 60 wt % of glucose. $V_{max}$ and $K_m$ would be larger if they were derived from the Eadie-Hofstee as shown in FIG. 11e or the Hanes-Woolf plots. However, $V_{max}$ and $K_m$ would be associated with the matrix pore size in the same manner regardless of which of the three plots were used. That is, both $V_{max}$ and $K_m$ increased with pore diameter of the matrices. But, $V_{max}$ for the immobilized ACP was smaller than that of free ACP while $K_m$ was larger than that of the free enzyme. This is in agreement with the expected effect of immobilization on the apparent $V_{max}$ and $K_m$ values.

The curves in the Eadie-Hofstee plots (FIG. 11e) are not linear over the whole range, but have apparent inflections. Without wishing to be bound by theory, it is postulated that if the reactions were run at optimal pH, the internal diffusional limitations would be more pronounced. The use of a substrate with larger molecular dimension than pNPP would also amplify the passive diffusional resistances.

The pH profile for free ACP in solution, and for immobilized ACP is included in Table 3. Table 3 shows that both free and immobilized ACP have similar pH profiles, with optimal pH 5.0. No shifting in optimal pH for the immobilized ACP was observed. This result is in agreement with the reported value of optimal pH 5.0 for wheat germ ACP indicating neither significant electrostatic interactions between the matrix and the enzyme nor the occurrence of significant pH difference inside and outside the matrix. Table 3 also clearly demonstrates that the apparent activities for all samples in the pH range 4.0–5.9 are related to the matrix pore diameters which are associated with concentration of D-glucose used in the preparations. The immobilized ACP activities under different pH values display similar dependence on glucose concentration as previously discussed. The relative activity among the immobilized ACP samples was basically independent of the pH of assay mixture, indicating the apparent activity is limited by the mass transport barrier of the matrix.

The improvement in thermal stability of enzymes due to immobilization is presumed to be caused by restricting the segmental motion of protein chains, driven by the gain of entropy by freeing of bound water, so as to reduce the possibility of an irreversible structure change, or by reducing denaturing segmental collision with the surface of the host through attachment to the surface. Evaluation of the stability of ACP from wheat germ showed loss of activity was the result of surface inactivation together with a sensitivity to dilution.

After heating at 50° C., in a pH 6.2 citrate buffer for one hour in the assay mixture without adding pNPP, and then cooling to room temperature, both immobilized and free ACP exhibited decreased apparent activity. For the dissolved ACP, it retained about 15 % of its initial activity while assayed at [pNPP]=5.0 mmol/L and pH 6.2 at room temperature. For the immobilized ACP biogels, the apparent activities were 44–87 % of the samples without thermal treatment, depending on the amount of glucose employed in the synthesis of the individual samples. The specific enzyme activity and percentage activity remaining for the ACP free and immobilized ACP are included below in Table 4.

TABLE 4

| Sample | Specific Activity @23° C. μmol/min.-mg) | Specific Activity @50° C. μmol/min.-mg) | Specific Activity @70° C. μmol/min.-mg) | Relative Activity 50° C./ 23° C. (%) | Relative Activity 70° C./ 23° C. (%) |
|---|---|---|---|---|---|
| ACP free | $8.29 \times 10^{-1}$ | $1.24 \times 10^{-1}$ | $4.52 \times 10^{-4}$ | 15 | 0 |
| AMAC0 | $6.66 \times 10^{-3}$ | $5.80 \times 10^{-3}$ | $2.31 \times 10^{-4}$ | 87 | 3 |
| AMAC10 | $6.57 \times 10^{-3}$ | $4.16 \times 10^{-3}$ | $8.03 \times 10^{-5}$ | 63 | 1 |
| AMAC20 | $5.34 \times 10^{-3}$ | $3.66 \times 10^{-3}$ | $1.27 \times 10^{-4}$ | 69 | 2 |
| AMAC30 | $8.16 \times 10^{-3}$ | $4.37 \times 10^{-3}$ | $-1.06 \times 10^{-4}$ | 54 | -1 |
| AMAC36 | $9.35 \times 10^{-3}$ | $4.15 \times 10^{-3}$ | $3.19 \times 10^{-4}$ | 44 | 3 |
| AMAC42 | $1.19 \times 10^{-2}$ | $5.35 \times 10^{-3}$ | $3.07 \times 10^{-4}$ | 45 | 3 |
| AMAC50 | $1.68 \times 10^{-2}$ | $7.44 \times 10^{-3}$ | $3.04 \times 10^{-4}$ | 44 | 2 |
| AMAC55 | $2.06 \times 10^{-2}$ | $1.06 \times 10^{-2}$ | $3.65 \times 10^{-5}$ | 51 | 0 |
| AMAC60 | $2.48 \times 10^{-2}$ | $1.63 \times 10^{-2}$ | $4.57 \times 10^{-4}$ | 66 | 2 |

Table 4 shows that thermal stability of ACP remarkably improved upon immobilization. Among the gel-immobilized ACP, the glucose-free sample displayed the highest percentage retention of activity (87%) after treatment at 50° C. in citrate buffer for one hour. The thermal stability of immobilized ACP prepared in the presence of glucose did not surpass that of the glucose-free sample. The samples made with either low (30% or below) or high concentration (55–60 wt %) of glucose showed over 50% of their initial activities after treatment at 50° C. for one hour.

TABLE 3

| | Apparent Activity (μmol/mg.-min.) pH Level | | | | | |
|---|---|---|---|---|---|---|
| Sample | 4 | 4.56 | 4.9 | 5 | 5.17 | 5.9 |
| ACP Free | 0.122 | 0.136 | 0.235 | 0.596 | 0.178 | 0.155 |
| AMAC0 | $1.61 \times 10^{-3}$ | $2.49 \times 10^{-3}$ | $4.94 \times 10^{-3}$ | $5.12 \times 10^{-2}$ | $2.14 \times 10^{-3}$ | $1.42 \times 10^{-3}$ |
| AMAC10 | $8.28 \times 10^{-4}$ | $8.85 \times 10^{-4}$ | $6.64 \times 10^{-3}$ | $4.77 \times 10^{-2}$ | $9.56 \times 10^{-4}$ | $9.32 \times 10^{-4}$ |
| AMAC20 | $1.25 \times 10^{-3}$ | $7.78 \times 10^{-4}$ | $5.70 \times 10^{-3}$ | $6.08 \times 10^{-2}$ | $6.75 \times 10^{-4}$ | $6.63 \times 10^{-4}$ |
| AMAC30 | $1.01 \times 10^{-3}$ | $2.03 \times 10^{-3}$ | $5.86 \times 10^{-3}$ | $5.54 \times 10^{-2}$ | $1.83 \times 10^{-3}$ | $1.01 \times 10^{-3}$ |
| AMAC36 | $2.39 \times 10^{-3}$ | $2.93 \times 10^{-3}$ | $4.33 \times 10^{-3}$ | $5.30 \times 10^{-2}$ | $3.00 \times 10^{-3}$ | $1.87 \times 10^{-3}$ |
| AMAC42 | $1.68 \times 10^{-3}$ | $4.77 \times 10^{-3}$ | $8.44 \times 10^{-3}$ | $6.13 \times 10^{-2}$ | $3.96 \times 10^{-3}$ | $3.44 \times 10^{-3}$ |
| AMAC50 | $5.25 \times 10^{-3}$ | $7.37 \times 10^{-3}$ | $9.41 \times 10^{-3}$ | $7.98 \times 10^{-2}$ | $6.85 \times 10^{-3}$ | $6.69 \times 10^{-3}$ |
| AMAC55 | $8.33 \times 10^{-3}$ | $7.60 \times 10^{-3}$ | $1.27 \times 10^{-2}$ | $9.80 \times 10^{-2}$ | $8.02 \times 10^{-3}$ | $8.82 \times 10^{-3}$ |
| AMAC60 | $7.99 \times 10^{-3}$ | $1.84 \times 10^{-2}$ | $2.05 \times 10^{-2}$ | $1.24 \times 10^{-1}$ | $1.65 \times 10^{-2}$ | $1.34 \times 10^{-2}$ |

Although the glucose-free sample maintained the highest percentage of its original activity among the immobilized ACP after heat treatment, the samples prepared with high concentration of glucose (50–60%) still showed greater apparent activities than the former, since the linear relationship between the apparent activities and pore volumes or diameters still held to some extent for the heat treated samples ($R^2$=0.93). Without wishing to be bound by theory, it is believed that the differences in enzymatic activity of ACP upon thermal treatment were associated with the degree of denaturation and the diffuision-controlled reaction rate. In immobilized ACP samples synthesized with low concentration of glucose, the pore volume or free space in the vicinity of ACP is relatively small. As such, in immobilized ACP samples, the free space surrounding the enzyme macromolecules in silica pores increases with glucose concentration.

On one hand, the large free space may increase the chance of denaturing segmental collision of ACP with the surface of the host during heat treatment and consequently result in lower thermal stability and enzymatic activity. On the other hand, the large free space in the near vicinity of the active site of ACP may improve catalytic activity through enhanced rate of mass transfer within the matrix, as previously discussed. Therefore, it is favorable to have relatively small free space surrounding the protein molecules in order to reduce the possibility of denaturing segmental collisions during thermal treatment but to have spacious channels to help ease of internal mass transport during assay. Compromise of these two factors leads to the trend in the thermal stability of immobilized ACP shown in Table 4. The results also demonstrate that the residual active enzyme macromolecules still converted the approaching substrate quite efficiently after 50° C. heat treatment for 1 hour, further illustrating the mass transport resistances of the carriers. However, extended heating may probably change the order of activity remaining owing to different rate and degree of thermal inactivation.

In addition, both free and immobilized samples did not show any remarkable catalytic activity (<3%) after treatment at 70° C. for one hour in the same solution as shown in Table 4. After put on the shelf in sealed vials for 70 days, the as-synthesized samples were estimated for enzymatic activity. The immobilized ACP retained 50–80% of its activities after exposure to room temperature for 10 weeks in comparison with samples kept in −15° C. freezer. The specific activity for the sample prepared with 60 wt % of glucose was about four times that of the glucose-free sample when assayed at pH 6.2 and [pNPP]=5.0 mmol, although the percentage retention of activity was about the same (74% for the glucose-free sample and 77% for the 60 wt % glucose biogel). Also, the loss of enzyme activity for the immobilized ACP after each cycle of assay was examined to find the operational stability. The assay was carried out once a day following the routine procedures. The sample was washed with water three times (3×15 ml) and kept at room temperature overnight in water after each assay. The percentage retention of activity in the third cycle, compared to that in the first cycle, was 80% for the glucose-free sample, and 80, 90 and 98% for the samples made, respectively, with 50, 55 and 60 wt % of glucose. The loss in activity for the other samples was larger after each cycle of assay.

Leaching of protein molecules from the porous silica host is not impossible when some biogels are immersed in an aqueous solution for an extended period of time. In this Example, it was found that the glucose-containing samples did not show lowered activities after intensive extraction with water (3×10 ml water for 30–80 milligrams of samples, one houw interval between two washes), when compared to the same samples with one time 5 ml of water extraction at room temperature prior to activity assay. Thus, ACP was effectively entrapped in porous silica matrices whether or not D-glucose was added in the sample preparations. In order to further investigate the possibility of leakage of ACP from the matrix during the assay process, a portion of the supernatant was separated from the assay system by centrifugation and decantation when the activity assay was completed. The change in p-nitrophenol concentration in the separated supernatant was evaluated and compared to that in the control group due to autohydrolysis of pNPP under the assay condition. No significant enzymatic activity (<4%) in the supernatant was detected and hence leaching of ACP from the silica matrix under the assay conditions was considered negligible. The fact that no leakage is detected is accountable when one considers the molecular weight of the ACP protein macromolecules obtained from wheat germ is over 50,000.

Based on the above data, in this Example, ACP was directly immobilized in microporous and mesoporous silica glasses without leakage via sol-gel processing. The immobilized ACP retained 7–22% of its native activity at its optimal pH 5.0, depending on the glucose concentration used in the preparation of the biogels. D-glucose served as an appropriate pore-forming material for the synthesis of silica gel-immobilized biologically active agents. The addition of glucose as the pore forming material not only modified the pore structure parameters but also enhanced the apparent activity of the immobilized enzyme. The pore size and pore volume of the silica matrix, as well as the catalytic activity of the immobilized ACP, increased with the concentration of glucose in the preparations. By controlling the amount of glucose used, the enzymatic reactivity of the immobilized biocatalyst could be regulated to the required level. Because D-glucose is an economical and environmentally-friendly pore forming material with good biocompatibility with enzymes, it may be widely used in the preparation of immobilized biologically active agents via the sol-gel reactions described herein in accordance with the invention.

Compared to sol-gel biocatalysts prepared in the absence of glucose, mesoporous biogels with increased pore size, pore volume and mesopore surface area formed in accordance with the invention exhibit improved catalytic activity owing to greater mass transfer of chemicals within the pores. First, this is of great importance in applications requiring monolithic or bulky bioglasses. Secondly, the increased pore size in the mesoporous matrix makes penetration of relatively large substrates within the gel possible due to reduced steric hindrance. Thirdly, the mesoporous materials provide an effective shell which may prevent the migration of protein macromolecules into or out of the open pores. As such, leaching of the immobilized enzyme from the host is prevented and the there is further prevention against attack of foreign enzymes like proteases. Finally, by controlling the amount of pore forming material, the mesoporous matrix with can achieve a specified pore diameter and relatively narrow pore distribution, which likely causes the preferable absorption and selective reaction of molecules with critical sizes.

This Example also demonstrates that it is very difficult, if not impossible, to determine the degree of denaturation or activity remaining of an enzyme after immobilization in a highly crosslinked organic-inorganic matrix since the activity assay only gives the overall apparent activity, controlled by internal diffusion-limited kinetics, that is often used to estimate the activity remaining. The true extent of deactivation or activity remaining of an enzyme upon immobilization in a porous carrier might be ascertained if one can find a proper homogenizing method. It shall be pointed out that the immobilization of ACP in this Example is only an illustration of principles of this novel improved synthesis technique and the preparation conditions may be further optimized to achieve higher retention of ACP activity or to immobilize other biologically active materials.

EXAMPLE 4

Horseradish peroxidase (HRP) was directly immobilized in mesoporous silicon-based matrices using the procedure for sol-gel reactions as described in Example 3 in the presence of various pore forming materials according to the invention, including D-fructose (samples FH16–FH60), D-glucose (Samples GH33 and GH42), sucrose (Samples SH33 and SH42), and glycerol (Samples YH33 and YH42). The percentage of each pore forming material is expressed below in Table 5 based on the amount of silicon dioxide and organic compound, along with the mean $V_{max}$ based on the average $V_{max}$ from the Eadie-Hofstee plot and the Hanes-Woolf plot, as described in other Examples herein. Table 5 also provides the standard deviation for the $V_{max}$ data. Table 5 also sets forth the mean $K_m$ value, as described in other Examples herein, based on average $K_m$ from the Eadie-Hofstee plot and the Hanes-Woolf plot, including the standard deviations for this data.

The apparent catalytic activities of the entrapped enzyme, as set forth in Table 5, showed up to more than 20% of the free HRP when assayed with a calorimetric method using 4-aminoantipyrine (4-AAP)-phenol (PHOH)-hydrogen peroxide ($H_2O_2$) reagents at a pH of 6.5 and room temperature. The activity was also measured as activity remaining after the sample underwent thermal treatment at 60° C. for 30 minutes before assaying at room temeprature, in comparison with the corresponding sample without thermal treatment as set forth as "Activity Remaining" in Table 5. Free HRP in solution retained 50% of its activity after such thermal treatment. Table 5 also includes the dry mass (g) of the total as-synthesized dry samples obtained after drying in vacuum at room temperature.

The experimental data demonstrated that immobilized HRP exhibited maximum activities at a higher concentration of hydrogen peroxide than free enzyme, due to the substrate, hydrogen peroxide, inhibition and diffusion limitation within the matrix pores. The matrices, obtained from removal of the pore forming materials set forth above from the sol-gel matrices formed and dried, using water extraction at room temperature, had interconnecting mesopore structures, as evidenced by nitrogen sorption measurements conducted using nitrogen adsorption-desorption isotherms at −196° C. on an ASAP 2010 as described above. The measurement data are provided in Table 6. The type of isotherms generated in accordance with such procedures as described in the other Examples herein are also listed in Table 6. The mesoporous structures and pores prevented leaching of HRP from the mesoporous materials and provided easy access to low molecular weight reactants. The catalytic activities of immobilized HRP were found to be closely related to the pore sizes and volumes of the mesoporous matrix materials which, in turn, were associated with the concentration of the pore forming compounds used in the synthesis of the composite biogels in accord with the findings of Example 3. Thermal stability of HRP upon immobilization was greatly improved. This Example and Example 3 demonstrate that the synthesis of mesoporous materials having immobilized biologically active agents using the pore forming materials of the invention provide versatility in terms of the biologically active agents and pore forming compounds, and indicate usefulness of these immobilized biologically active agents as various biocatalysts and biosensors.

TABLE 5

| Sample | $V_{max}$ (units/mg-min) | $K_m$ (mol/L) | Activity Remaining (%) | Dry Mass (g) |
|---|---|---|---|---|
| FH0 | 0.156 (±0.067) | (2.04 ± 0.79) × 10⁻⁴ | 146 | 1.381 |
| FH16 | 0.699 (±0.045) | (4.57 ± 0.76) × 10⁻⁴ | 134 | 1.615 |
| FH33 | 25.3 (±1.3) | (7.20 ± 0.81) × 10⁻⁴ | 123 | 2.020 |
| FH42 | 146.6 (±3.0) | (9.90 ± 0.46) × 10⁻⁴ | 113 | 2.399 |
| FH50 | 173.7 (±12.7) | (9.24 ± 1.22) × 10⁻⁴ | 112 | 2.732 |
| FH60 | 57.1 (±7.7) | (4.73 ± 1.5) × 10⁻⁴ | 110 | 3.477 |
| GH33 | 46.4 (±0.7) | (7.90 ± 0.18) × 10⁻⁴ | 131 | 2.040 |
| GH42 | 155.5 (±6.0) | (1.10 ± 0.08) × 10⁻³ | 102 | 2.366 |
| SH33 | 59.4 (±1.1) | (1.05 ± 0.04) × 10⁻³ | 134 | 2.021 |
| SH42 | 171.4 (±11.6) | (1.16 ± 0.13) × 10⁻³ | 107 | 2.324 |
| YH33 | 0.373 (±0.040) | (2.0 ± 0.2) × 10⁻⁴ | 118 | 1.952 |
| YH42 | 94.0 (±5.9) | (8.24 ± 1.0) × 10⁻⁴ | 120 | 2.240 |

TABLE 6

| Sample | Isotherm | Specific Surface Area ($m^2/g$) | | | Specific Pore Volume ($m^3/g$) | | | Pore Diameter (Å, 4V/A) | | |
|---|---|---|---|---|---|---|---|---|---|---|
| | | BET | $BJH_{Ads}$ | $BJH_{Des}$ | Single Point | $BJH_{Ads}$ | $BJH_{Des}$ | BET | $BJH_{Ads}$ | $BJH_{Des}$ Peak |
| FH0 | I/IV | 738 | 467 | 434 | 0.449 | 0.334 | 0.262 | 24.3 | 28.6 | |
| FH16 | I/IV | 706 | 379 | 353 | 0.416 | 0.269 | 0.207 | 23.6 | 28.4 | |
| FH33 | IV/H2 | 736 | 565 | 527 | 0.492 | 0.429 | 0.337 | 26.7 | 30.3 | 32.5 |
| FH42 | IV/H2 | 738 | 782 | 746 | 0.642 | 0.714 | 0.553 | 34.8 | 36.5 | 34.0 |
| FH50 | IV/H2 | 652 | 743 | 755 | 0.762 | 0.805 | 0.700 | 46.7 | 43.4 | 43.3 |
| FH60 | IV/H2 | 682 | 760 | 750 | 0.750 | 0.799 | 0.671 | 44.0 | 42.0 | 38.5 |
| GH33 | IV/H2 | 711 | 575 | 548 | 0.516 | 0.467 | 0.366 | 29.0 | 32.5 | 32.4 |
| GH42 | IV/H2 | 637 | 682 | 689 | 0.636 | 0.692 | 0.553 | 39.9 | 40.6 | 34.7 |
| SH33 | IV/H2 | 691 | 603 | 583 | 0.516 | 0.491 | 0.403 | 29.9 | 32.5 | 32.4 |
| SH42 | IV/H2 | 747 | 683 | 676 | 0.601 | 0.587 | 0.489 | 32.2 | 34.4 | 33.6 |
| YH33 | IV/H2 | 786 | 558 | 514 | 0.503 | 0.415 | 0.318 | 25.6 | 29.7 | 31.7 |
| YH42 | IV/H2 | 879 | 689 | 640 | 0.562 | 0.525 | 0.417 | 27.5 | 30.5 | 32.4 |

EXAMPLE 5

In this Example, various preferred pore forming materials were used to make mesoporous materials, specifically D-glucose, dibenzoyl-L-tartaric acid, and D-maltose. Upon removing the pore forming materials, it was found that mesoporous materials were achieved. The samples were analyzed using XRD diffraction patterns which suggested a disordered channel assembly. The pore diameters achieved varied from 20 Å to about 60 Å depending upon pore forming material concentration.

The organometallic compound used to form the mesoporous material in this Example was tetraethylorthosilicate. The tetraethylorthosilicate was dissolved in an ethanol solution and combined with distilled water and a hydrochloric acid as the acid catalyst in molar ratios of tetraethylorthosilicate:water:catalyst:ethanol of 1:4:0.01:3. The reactants were prehydrolyzed at 60° C. for about 1–2 hours, during which the initial phase-separation disappeared and the mixture became homogeneous. This was followed by reflux for 2 hours. After cooling to room temperature, the solution was combined with an aqueous solution of D-glucose (0.8 mol/l), an aqueous solution of D-maltose (1.2 mol/l) or an ethanol solution of dibenzoyl-L-tartaric acid (0.3 mol/l) while stirring. The homogeneous solutions obtained were cast into cylindrical polystyrene molds followed by sealing of the molds with a cover having 2–3 pinholes for allowing evaporation of volatile solvents and byproducts.

The reaction was allowed to stand at room temperature for gelation and slow drying for 15–20 days to provide a colorless, transparent (>80% transmission in visible light range), monolithic disk of the pore forming compound-containing silicon-based matrix. The mesoporous materials were formed by removing the pore forming materials. The materials were removed by first grinding the disks to fine powder, followed by Soxhlet extraction with methanol or water for 2–3 days followed by drying at 100° C. overnight. The extent of pore forming material removed was monitored using TGA as described above for weight loss at 750° C. at which the pore forming materials decomposed completely.

The BET surface areas and pore volumes were determined before and after extraction by nitrogen adsorption-desorption isotherm measurements. The unextracted samples had relatively small BET surface areas and pore volumes. Upon extraction, the surface areas and pore volumes increased drastically. The surface areas were found to correlate linearly with the extent of pore forming material removed at various extraction times. For example, the surface are of Sample DB40 in Table 7 having about 40 wt % dibenzoyl-L-tartaric acid changed linearly from 2.7 m²/g before the extraction to 926 m²/g after total removal of the dibenzoyl-L-tartaric acid after 3 days extraction.

The BET surface area data and pore parameters of the samples after the removal of the pore forming materials are summarized in Table 7. In general, an increase in the concentration of the pore forming materials in the mesoporous materials resulted in greater BET surface area and pore volume after extraction. In the case of dibenzoyl-L-tartaric acid, as the concentration was increased to 43 wt %, the surface area reached to nearly 1000 m²/g, beyond which the effect of concentration appeared to stagnate. The pore volume rose continuously from 0.159 to 0.998 cm³/g as the concentration of the dibenzoyl-L-tartaric acid increased from 8 to 57 wt %. The surface area of 100 m²/g and the pore volume greater than 0.5 cm³/g are among the indications of formation of mesopores in the structure. While both micropores and mesopores contribute to structure, the contribution of mesopores increases with pore forming material concentration and dominate at concentrations of about 30 to 40 wt % and higher.

Figure 12:
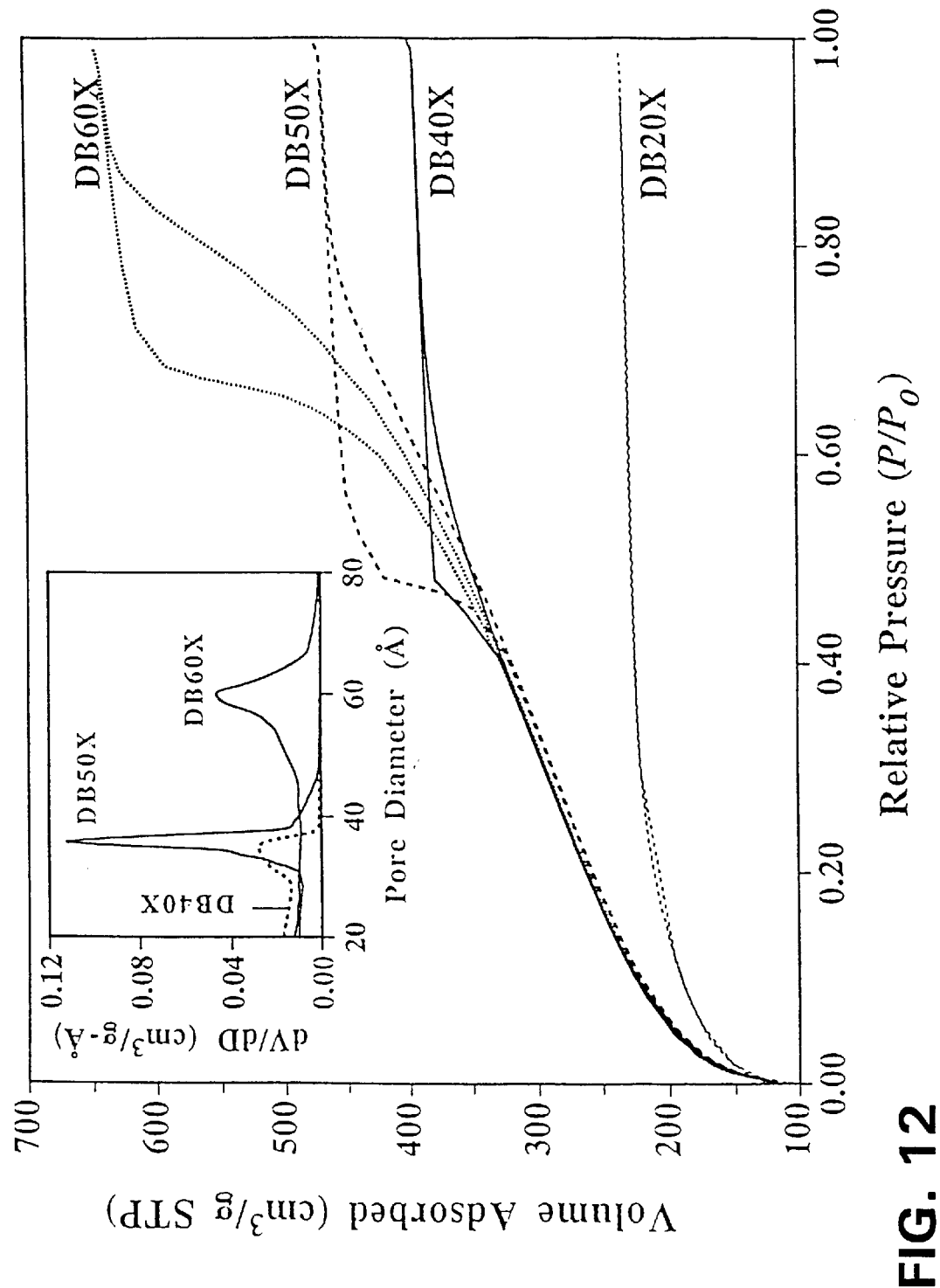
FIG. 12 is a graphical representation of the nitrogen adsorption-desorption isotherms determined at various relative pressures ($P/P_o$) on the mesoporous material samples in Example 5 including an inset which is a graphical representation of the derived BJH desorption pore size distributions.

The nitrogen adsorption-desorption isotherms were determined at various relative pressures ($P/P_o$) on the mesoporous material samples. As shown in FIG. 12, the samples DB40X, DB50X, and DB60X prepared with high dibenzoyl-L-tartaric acid concentrations of ≧40 wt % exhibited Type IV isotherms with Type H2 hysteresis loops, whereas sample DB20X prepared with low pore forming concentration of dibenzoyl-L-tartaric acid of 16 wt % shows a completely reversible Type I isotherm, typical of microporous structures. The position of the well-defined step in the nitrogen desorption isoterms appears to shift to higher relative pressures as the pore forming material concentration is increased. These characteristics are similar to those observed for prior art surfactant pore formers and can be attributed to capillary condensation within narrow tubular mesopores of 30–60 Å in effective diameter such that the pores may be tubular. Furthermore, the ratio of pore volume to surface area in this Example was found to be close to one half the average radius as indicated by $(V/S_{BET})/(r_{av}/2)$ values approximating unity which is in agreement with tubular channels of average radius.

The pore size and its distribution were also found to be influenced by concentration of pore forming materials as shown in FIG. 12. As the concentration of pore forming material increased from 43 to 57 wt %, the dominant pore diameter increased from about 34 to 60 Å. The fidelity of pore distribution, as indicated by the width at half height of the peak, ranges from 3 to 8 Å, which is comparable to values achieved using surfactant pore formers. The type and size of pore forming materials seemed to have relatively less effect on the pore size distribution, for example, at approximately the same pore forming concentration (50 wt %), the D-glucose and D-maltose formed mesoporous structures (DB50X and MT50X, respectively) have almost identical BJH pore size distributions although their molecule sizes are very different. The variation in the pore diameter is only 4 Å between DB50X and MT50X as shown in Table 7. These observations differ from similar observations based on surfactant pore forming materials.

Figure 13:
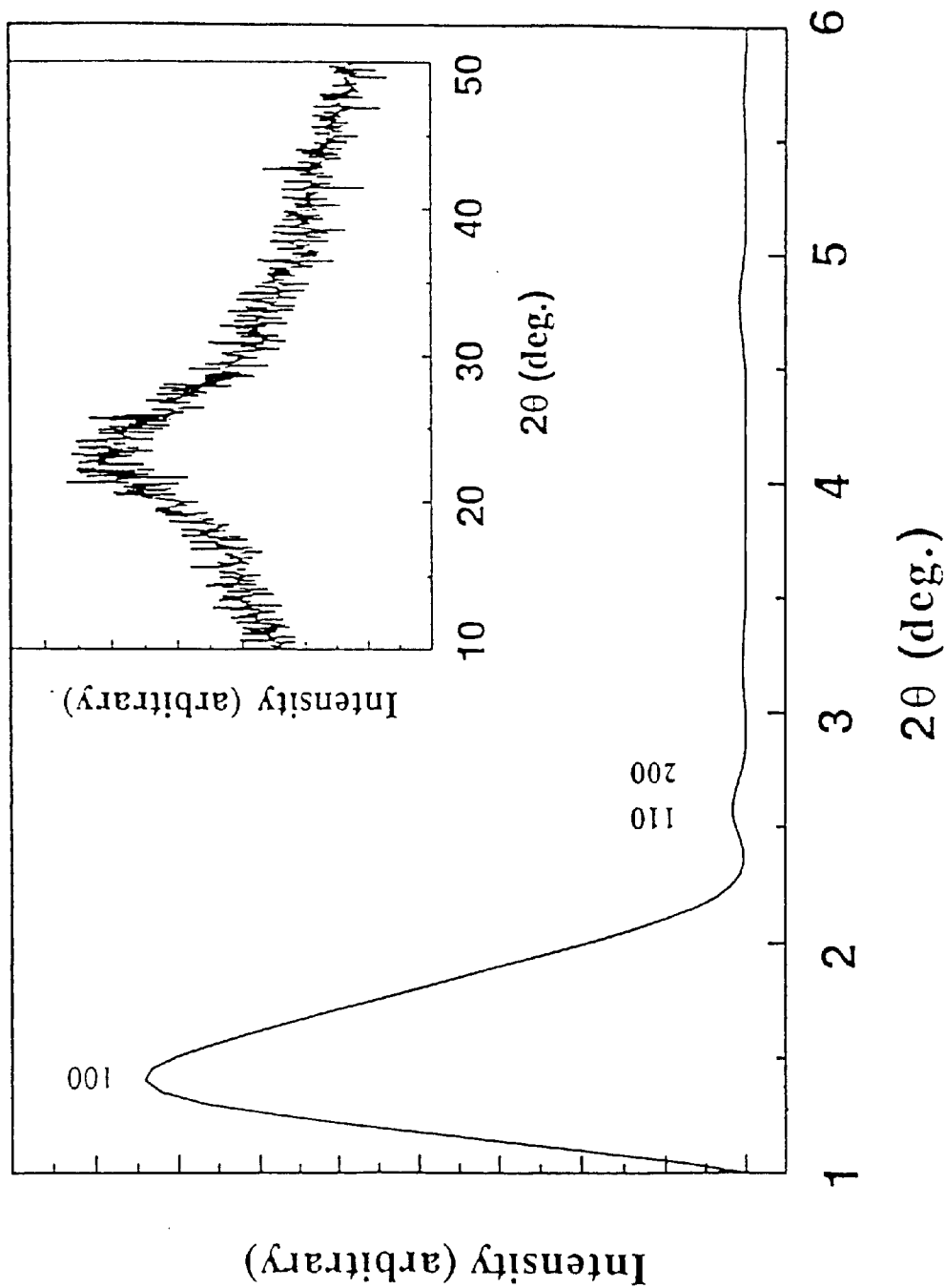
FIG. 13 is a representation of the XRD patterns of the mesoporous materials prepared with 48% of D-maltose in Example 5.

The XRD pattern of the mesoporous materials prepared with 48% of D-maltose is shown in FIG. 13. The pattern appears to have a peak (100 reflection) with a d-spacing of 62 Å and a broad, low intensity peak (d of about 35–31 Å) which could possibly be caused from overlapped 110 and 200 reflections. Such a pattern is consistent with mesoporous structures. Consideration of the thickness of the pore walls would indicate that the d-spacing value for the 100 reflection is comparable to the BJH pore diameter (32 Å). There was a typical amorphous silica halo at a 2θ value of about 23° (insert of FIG. 13) for the matrix before and after removal of the pore forming material by extraction indicating the amorphous nature of the sol-gel silica matrix. In addition, the lack of distinct XRD peaks except for the amorphous halo in the materials before extraction suggests that the pore forming materials did not crystallize during or after the sol-gel processing. Calcination of the extracted matrix at 500° C. for 5 hours resulted in little change in the amorphous halo, but a slight decrease of about 2–5 Å in the pore diameter, common for silica mesoporous structures formed by sol-gel processes. Substantial mesostructures remained even after calcination at 900° C. for 5 hours in air.

Figure 14:
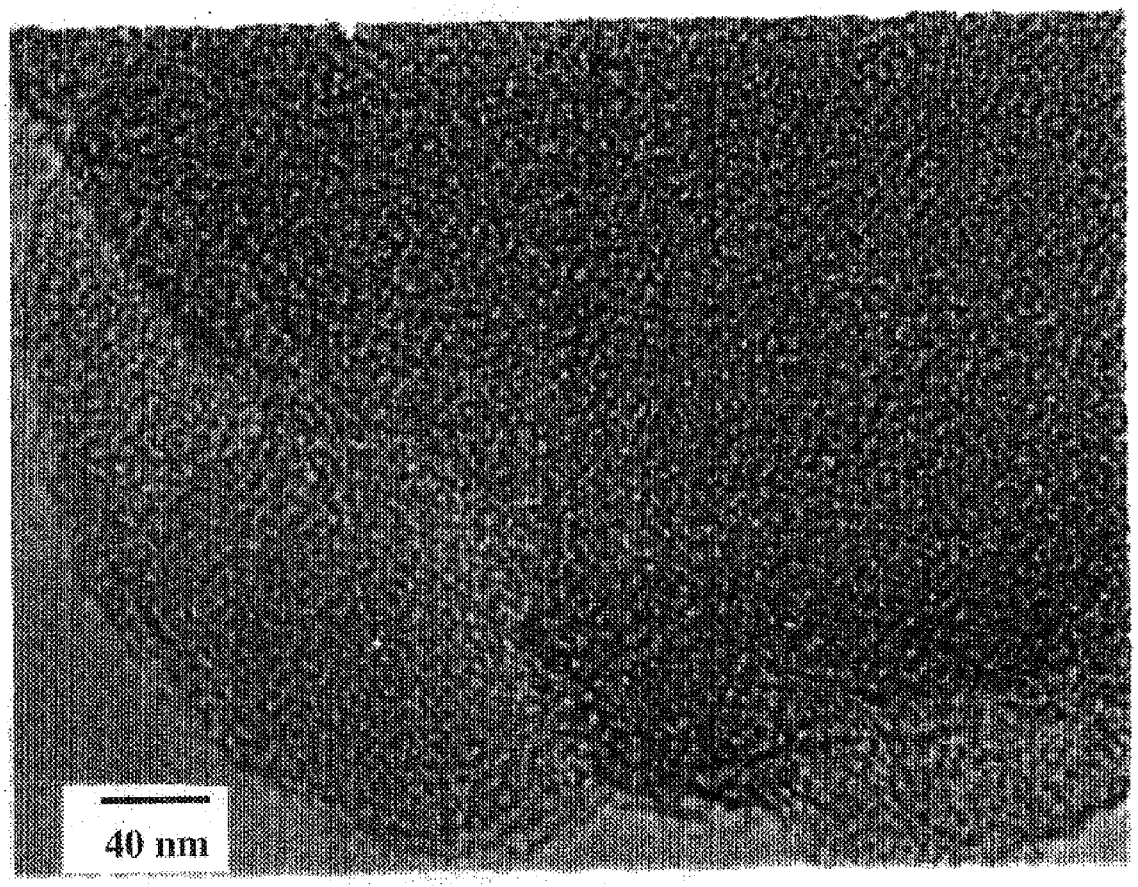
FIG. 14 is a representation of TEM micrograph for sample DB50X prepared with 50 wt % dibenzoyl-L-tartaric acid in Example 5.

A typical TEM micrograph is shown in FIG. 14 for sample DB50X prepared with 50 wt % dibenzoyl-L-tartaric acid. There are numerous cylindrically shaped channels, which are regular in diameter. Thus, the aggregation or assembly of the aggregates of the pore forming materials appears to play an important role and hydrogen bonding between the aggregated pore forming materials and inorganic intermediates in solution and/or during gelation likely contributes to mesophase formation as described above. Such aggregation should still remain at molecular levels without crystallization and have small dimensions, i.e.,<400 nm as evidenced by the fact that the matrices having the pore forming materials exhibited powder XRD patterns of typical amorphous materials and were transparent to visible light. The dimension of the aggregates increases with the concentration of the pore forming materials, thereby affecting the size of the mesopores. However, at very high concentrations, i.e., greater than 60 wt %, some crystallization was observed.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

TABLE 7

| Sample | Pore Forming Material | Pore Forming Material (wt %) | Surface Area ($S_{BET}$) ($m^2/g$) | Pore Volume ($V_p$) ($cm^3/g$) | BJH Pore Diameter (Å) | Ratio of ($V_p/S_{BET}$) to ($r_{av}/2$) | Micropore Volume ($cm^3/g$) | Micropore Surface Area ($m^2/g$) |
|---|---|---|---|---|---|---|---|---|
| DB05X | DBTA | 4 | 286 ± 7 | 0.154 | — | — | 0.120 | 238 |
| DB10X | DBTA | 8 | 278 ± 7 | 0.159 | — | — | 0.121 | 218 |
| DB20X | DBTA | 16 | 668 ± 17 | 0.360 | — | — | 0.171 | 320 |
| DB40X | DBTA | 43 | 926 ± 7 | 0.615 | 34 | 0.99 | 0.054 | 122 |
| DB50X | DBTA | 49 | 884 ± 10 | 0.735 | 36 | 1.06 | 0.054 | 100 |
| DB60X | DBTA | 57 | 901 ± 10 | 0.998 | 60 | 1.00 | 0.048 | 89 |
| DG10X | D-glucose | 9 | 455 ± 12 | 0.250 | — | — | 0.184 | 343 |
| DG20X | D-glucose | 16 | 525 ± 17 | 0.305 | — | — | 0.195 | 329 |
| DG40X | D-glucose | 37 | 980 ± 10 | 0.565 | 18 | 0.97 | 0.002 | 14 |
| DG50X | D-glucose | 45 | 1047 ± 2 | 0.732 | 32 | 1.06 | 0 | 0 |
| MT30X | D-maltose | 32 | 617 ± 11 | 0.342 | 16 | 0.95 | 0.057 | 108 |
| MT50X | D-maltose | 48 | 1016 ± 5 | 0.696 | 32 | 1.01 | 0 | 0 |

We claim:

1. A method for making a mesoporous material comprising:
   (a) forming an aqueous solution having an organometallic compound;
   (b) adding a solution to the aqueous solution, the added solution comprising a pore forming material selected from the group consisting of monomeric polyols, polyacids, polyamines, carbohydrates, oligopeptides of at least two amino acid units, oligonucleic acids, carbonyl functional organic compounds, and mixtures and derivatives thereof to form a sol gel matrix by polycondensation;
   (c) drying the sol gel matrix; and
   (d) removing the pore forming material from the dried sol-gel matrix to thereby form a mesoporous material.

2. The method of claim 1, wherein the mesoporous material is formed such that substantially all pores are mesopores, a mixture of mesopores and micropores, or a mixture of mesopores and macropores.

3. The method according to claim 1, wherein the pore forming material interacts by polar or hydrogen bonding with intermediates of the organometallic compound in the sol-gel matrix.

4. The method according to claim 1, wherein step (a) further comprises forming the aqueous solution having the organometallic compound by hydrolyzing at least one metal alkoxide.

5. The method according to claim 4, wherein the at least one metal alkoxide is selected from the group consisting of tetramethylorthosilicate and tetraethylorthosilicate.

6. The method according to claim 4, further comprising hydrolyzing that is acid catalyzed.

7. The method according to claim 6, further comprising hydrolyzing that is acid catalyzed using hydrochloric acid as an acid catalyst.

8. The method according to claim 4, further comprising hydrolyzing that is base catalyzed.

9. The method according to claim 8, further comprising hydrolyzing that is base catalyzed using sodium hydroxide as a base catalyst.

10. The method according to claim 1, wherein the pore forming material is a non-surfactant, polar compound which forms a hydrogen bond in the sol-gel matrix.

11. The method according to claim 1, wherein the pore forming material is selected from the group consisting of D-glucose, D-maltose, D-fructose, sucrose, dibenzoyl-L-tartaric acid, cyclodextrins, and soluble starches.

12. The method according to claim 1, wherein the mesoporous material has pores which are substantially all mesoporous and step (b) further comprises adding the pore forming material in an amount effective to provide an average pore diameter of from about 20 Å to about 100 Å in the mesoporous material.

13. The method according to claim 1, wherein step (b) further comprises adding at least 20% by weight of the pore forming material based on the weight of the dried sol-gel matrix.

14. The method according to claim 13, wherein the pore diameter is from about 30 Å to about 60 Å.

15. The method according to claim 1, wherein step (c) further comprises drying the sol gel matrix by evaporation to form a solid matrix.

16. The method according to claim 15, further comprising grinding the solid matrix prior to removing the pore forming material from the solid matrix.

17. The method according to claim 1, wherein step (d) further comprises removing the pore forming material from the solid matrix by solvent extraction or calcination.

18. The method according to claim 17, further comprising removing the pore forming material from the solid matrix by solvent extraction and extracting with water as a solvent.

19. The method according to claim 1, wherein step (b) further comprises adding a biologically active agent.

20. The method according to claim 19, wherein the biologically active agent is added in solution form after adding the solution comprising the pore forming material.

21. A method for making a mesoporous material comprising:

(a) forming an aqueous solution having an organometallic compound;
(b) adding a solution to the aqueous solution, the added solution comprising a pore forming material which is a non-surfactant to form a sol gel matrix by polycondensation;
(c) drying the sol gel matrix; and
(d) removing the pore forming material from the dried sol-gel matrix to thereby form a mesoporous material.

22. The method of claim 1, further comprising controlling degree of mesoporosity and average diameter of mesopores by varying a concentration of the pore forming material.

* * * * *